(12) United States Patent
Barrett et al.

(10) Patent No.: US 12,171,804 B2
(45) Date of Patent: *Dec. 24, 2024

(54) METHODS OF TREATING CHEMOTHERAPY INDUCED NEUTROPENIA USING FIXED DOSES OF EFLAPEGRASTIM

(71) Applicant: Spectrum Pharmaceuticals, Inc., Irvine, CA (US)

(72) Inventors: John A. Barrett, Groton, MA (US); Sribalaji Lakshmikanthan, Boxborough, MA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 17/374,302

(22) Filed: Jul. 13, 2021

(65) Prior Publication Data
US 2022/0016212 A1 Jan. 20, 2022

Related U.S. Application Data

(60) Provisional application No. 63/053,333, filed on Jul. 17, 2020.

(51) Int. Cl.
*A61K 38/19* (2006.01)
*A61K 45/06* (2006.01)
*A61P 7/06* (2006.01)

(52) U.S. Cl.
CPC ............ *A61K 38/193* (2013.01); *A61K 45/06* (2013.01); *A61P 7/06* (2018.01)

(58) Field of Classification Search
CPC ................................ A61K 38/193; A61P 7/06
See application file for complete search history.

(56) References Cited

FOREIGN PATENT DOCUMENTS

WO    WO2019152530    *  8/2019   ........... A61K 31/496

OTHER PUBLICATIONS

National Cancer Institute—eflapegrastim. https://www.cancer.gov/publications/dictionaries/cancer-drug/def/eflapegrastim. accessed Apr. 17, 2024. (Year: 2024).*
Vacirca et al. (An open-label, dose-ranging study of Rolontis, a novel long-acting myeloid growth factor, in breast cancer. Cancer Medicine, 7, 1660-1669, 2018. (Year: 2018).*
Schwartzberg et al. Safety and efficacy of eflapegrastim in reducing sever neutropenia in patients treated with myelosuppressive chemotherapy in a phase 3 randomized controlled trial compared to pegfilgrastim (ADVANCE trial). J. Clin. Oncol. 36, No. 15, suppl . Abstract e12513, 2018. (Year: 218).*
Roskos, Lorin K. et al. "Pharmacokinetic/Pharmacodynamic Modeling of Pegfilgrastim in Healthy Subjects", J Clin Pharmacol 2006;46:747-757.

* cited by examiner

*Primary Examiner* — Elly-Gerald Stoica
(74) *Attorney, Agent, or Firm* — Global Patent Group Inc.; Lauren L. Stevens

(57) ABSTRACT

This disclosure provides a method of preventing, alleviating, or treating a condition (i.e., neutropenia) in a patient in need thereof, the condition characterized by compromised white blood cell production in the patient. The method includes administering to the patient a therapeutically effective amount of a protein complex comprising a modified human granulocyte-colony stimulating factor (hG-CSF) covalently linked to an immunoglobulin Fc region via a non-peptidyl polymer at a fixed dose regardless of the patient's weight.

9 Claims, 6 Drawing Sheets

Specification includes a Sequence Listing.

M. Size Marker
1. [17,65]Ser-G-CSF-PEG-Fc non-reducing conditions
2. [17,65]Ser-G-CSF-PEG-Fc reducing conditions
3. Use of anti-G-CSF antibody ([17,65]Ser-G-CSF-PEG-Fc non-reducing conditions)
4. Use of anti-G-CSF antibody ([17,65]Ser-G-CSF-PEG-Fc reducing conditions)

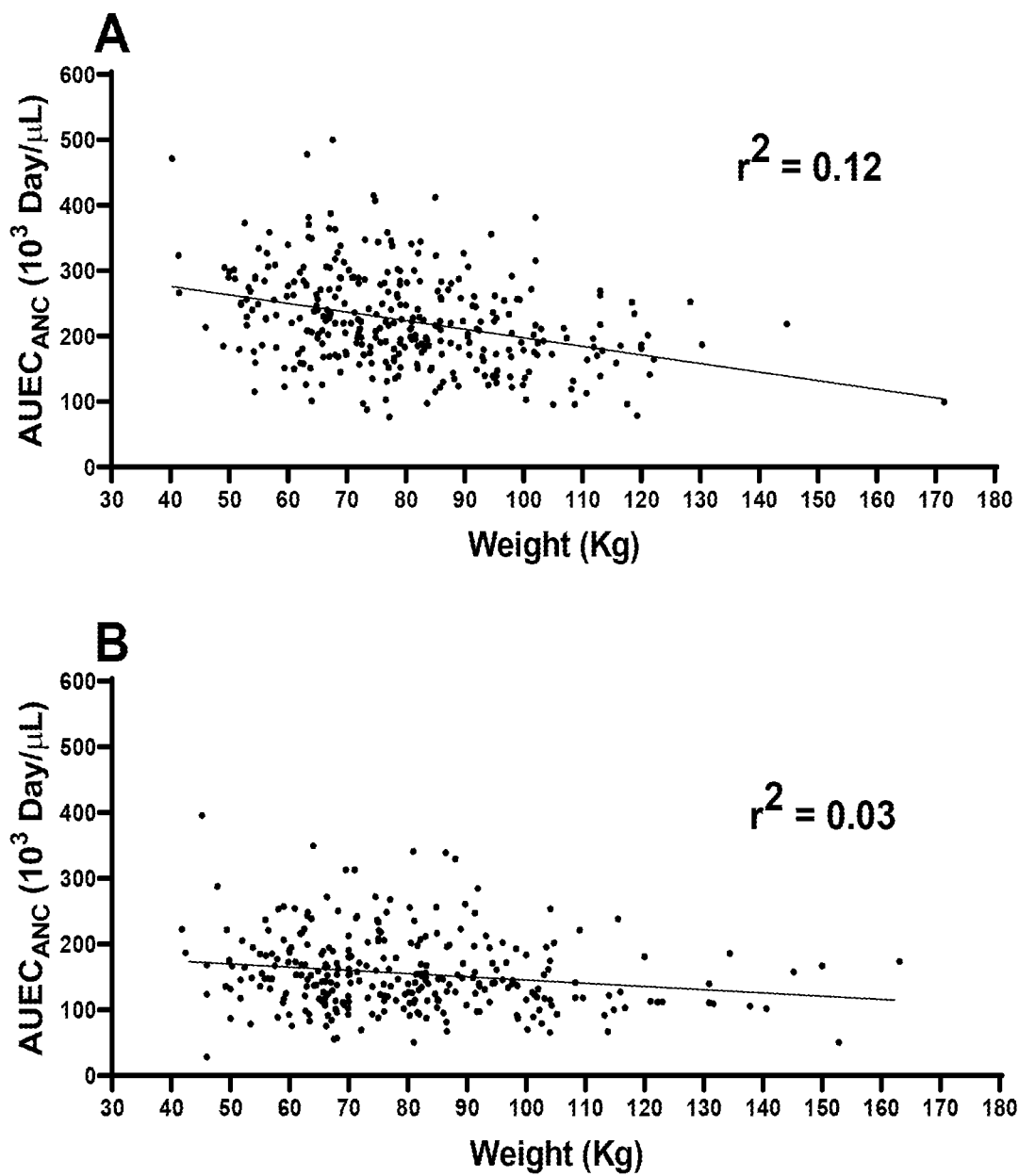
FIGS. 6 A and 6B

SEQUENCE LISTING

<160> NUMBER OF SEQ ID NOS: 2

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Ser Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 221
<212> TYPE: PRT
<213> ORGANISM: Homo sapiens

<400> SEQUENCE: 2

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln

```
            145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
                180                 185                 190

Glu Gly Asn Val Phe Ser Cys Ser Val Met His Glu Ala Leu His Asn
            195                 200                 205

His Tyr Thr Gln Lys Ser Leu Ser Leu Ser Leu Gly Lys
        210                 215                 220
```

METHODS OF TREATING CHEMOTHERAPY INDUCED NEUTROPENIA USING FIXED DOSES OF EFLAPEGRASTIM

CROSS-REFERENCE TO RELATED APPLICATIONS

This application claims priority under 35 U.S.C. § 119(e) to U.S. Provisional Patent Application No. 63/053,333, filed Jul. 17, 2020. The foregoing application is incorporated by reference herein in its entirety.

TECHNICAL FIELD

The present invention relates to use of G-CSF protein linked to an immunoglobulin Fc compositions for treating, preventing, or reducing the risk of developing chemotherapy-induced neutropenia at a fixed dose administered once per chemotherapy cycle.

BACKGROUND OF THE INVENTION

Chemotherapy-induced neutropenia is common toxicity caused by the administration of anti-cancer drugs. It is associated with life-threatening infections and may alter the chemotherapy schedule, thus impacting on early and long-term clinical outcome. Among others, it is frequently caused by chemotherapy regimens that includes agents such as docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). It usually leads to prolonged hospitalization, intravenous administration of broad-spectrum antibiotics, and is often associated with significant morbidity and mortality. About 25% to 40% of treatment naïve patients develop febrile neutropenia with common chemotherapy regimens in the absence of G-CSF support. The severity of neutropenia (depth of the neutrophil nadir after chemotherapy) and the duration of severe neutropenia (DSN) are correlated with the risk of developing febrile neutropenia, infectious complications, and hospitalization.

Current therapeutic modalities employ granulocyte colony-stimulating factor (G-CSF) and/or antibiotic agents to combat this condition. The first long-acting recombinant human G-CSF, pegfilgrastim)(Neulasta®, simplified supportive care for chemotherapy-induced neutropenia with a one dose-per-chemotherapy-cycle option. Since then, biosimilar products have become available, but supportive care options for chemotherapy-induced neutropenia have otherwise remained unchanged. Thus, there is still a strong need for new formulations and methods of use that can enhance patients' outcomes and improve supportive care options available to the patients.

SUMMARY OF THE INVENTION

The disclosure relates to the methods of using a G-CSF containing a more stable protein complex at doses that reduces the risk of developing neutropenia in patients in need thereof and maintaining a serum concentration that achieves the optimal therapeutic outcome.

In one aspect, this disclosure provides a method of preventing, alleviating or treating a chemotherapeutic induced condition a patient in need thereof. The method comprises administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In some embodiments, the chemotherapy induced condition is selected from the group consisting of: reduced hematopoietic function, reduced immune function, reduced neutrophil count, reduced neutrophil mobilization, mobilization of peripheral blood progenitor cells, sepsis, neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome.

In some embodiments, the chemotherapy induced condition is myelosuppression or neutropenia. In some embodiments, the neutropenia is severe chronic neutropenia or febrile neutropenia.

In some embodiments, the chemotherapy induced condition is characterized by compromised white blood cell production. In some embodiments, the compromised white blood cell production is a result of chemotherapy, radiation therapy, or idiopathic thrombocytopenia purpura.

In some embodiments, the EFLAPEGRASTIM is administered after the patient is treated with adjuvant or neoadjuvant chemotherapy. In some embodiments, the adjuvant or neoadjuvant chemotherapy comprises at least one of docetaxel and cyclophosphamide. In some embodiments, the adjuvant or neoadjuvant chemotherapy comprises a combination of docetaxel and cyclophosphamide.

In some embodiments, the EFLAPEGRASTIM is administered between 1 and 3 days after the patient is treated with adjuvant or neoadjuvant chemotherapy.

In some embodiments, a second dose of the EFLAPEGRASTIM is administered between 5 and 30 days after a first dose of the protein complex is administered to the patient. In some embodiments, the second dose of the EFLAPEGRASTIM is administered between 15 and 25 days after a first dose of the protein complex is administered to the patient.

In some embodiments, the therapeutically effective amount is a unit dosage form selected from 25 pg/kg, 50 pg/kg, 100 pg/kg, and 200 pg/kg. In some embodiments, the patient's weight ranges from 30 kg to 180 kg.

In some embodiments, the fixed dose is 13.2 mg. In some embodiments, the fixed dose is provided in a dosage volume of about 0.4 ml to about 1 ml. In some embodiments, the fixed dose is provided in a dosage volume of about 0.6 ml.

In some embodiments, the EFLAPEGRASTIM administered at a fixed dose of 13.2 mg regardless of patient's weight.

In some embodiments, the method comprises administering to the patient a therapeutically effective amount of a second agent. In some embodiments, the second agent is an anti-cancer agent. In some embodiments, the anti-cancer agent comprises a checkpoint inhibitor.

BRIEF DESCRIPTION OF THE DRAWINGS

FIGS. 6A and 6B show the dffect of body weight on the neutrophil response after administration of EFLAPEGRASTIM (N=331) (FIG. 6A) or pegfilgrastim (N=290) (FIG. 6B) 24 hours after docetaxel and cyclophosphamide chemotherapy. ($AUEC_{ANC}$, area under the absolute neutrophil count effect curve).

DETAILED DESCRIPTION OF THE INVENTION

Figure 1:
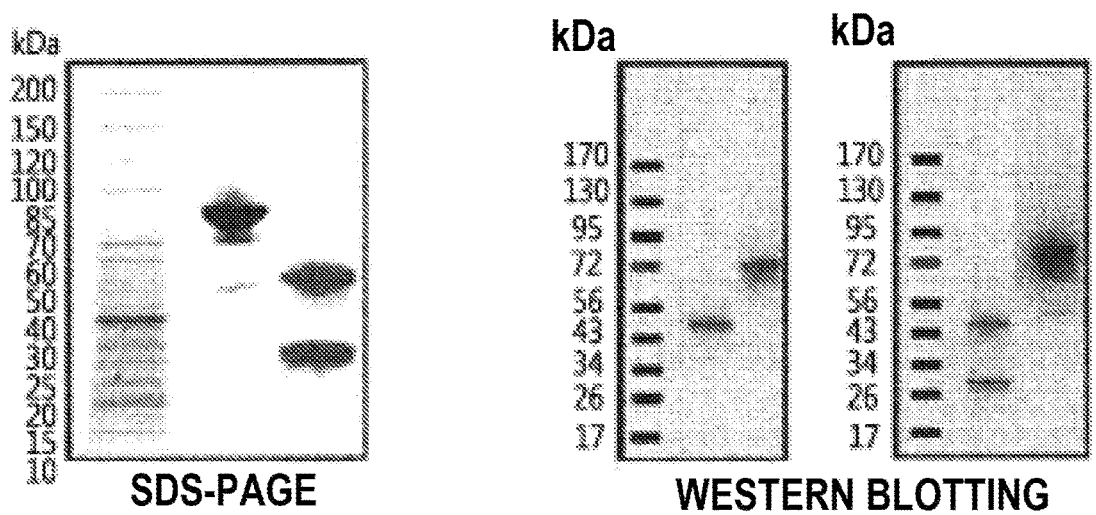
FIG. 1 shows a result of peptide mapping for analyzing Fc region N-terminal binding of a $^{17,65}$Ser-G-CSF-PEG-Fc complex which was prepared by N-terminal reaction of an immunoglobulin Fc region.

In one aspect, the present disclosure provides methods of preventing, alleviating, prophylactically treating, and treating a patient having a condition characterized by the compromised white blood cell production.

Methods of Prevention and Treatment

The method includes administering to the patient in need of such treatment a therapeutically effective amount of a protein complex comprising a physiologically active polypeptide, such as a modified human granulocyte-colony stimulating factor (hG-CSF), covalently linked to an immunoglobulin Fc region via a non-peptidyl polymer. The non-peptidyl polymer can be site-specifically linked to an N-terminus of the immunoglobulin Fc region, and the modified hG-CSF includes substitutions in at least one of Cys17 and Pro65.

In another aspect, the present disclosure provides a method for increasing the number of granulocytes in eligible patients for a bone marrow transplant. The method includes administering to the patient in need of such treatment a therapeutically effective amount of a protein complex comprising a modified hG-CSF covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65. In some embodiments, the protein complex is EFLAPEGRASTIM.

In yet another aspect, the present disclosure provides a method for increasing stem cell production in a patient. The method includes administering to the patient in need of such treatment a therapeutically effective amount of a protein complex comprising a modified human hG-CSF covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In yet another aspect, the present disclosure provides a method for increasing the number of hematopoietic progenitor cells in a patient in need that include those undergoing chemotherapy or those who are donors of stem cells to other patients. The method includes administering to the patient a therapeutically effective amount of a protein conjugate comprising a modified human hG-CSF covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In other aspects, the presently disclosed protein complex can be used for treatment of conditions including reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome. In one embodiment, the condition is myelosuppression, neutropenia, or preferably febrile neutropenia.

In another aspect, the present disclosure provides a method for preventing, alleviating, prophylactically treating, and treating infection as manifested by neutropenia (e.g., febrile neutropenia) in the patient with non-myeloid malignancies receiving myelosuppressive anti-cancer drugs. The method includes administering to the patient a therapeutically effective amount of a protein complex comprising a modified hG-CSF covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In certain embodiments, the modified G-CSF is by way of a substitution at Cys17 is Cys17Ser. In other embodiments, the substation at Pro65 is Pro65Ser.

In some embodiments, the chemotherapy induced condition is myelosuppression or neutropenia. In some embodiments, the neutropenia is severe chronic neutropenia or febrile neutropenia.

In some embodiments, the compromised white blood cell production is a result of chemotherapy, radiation therapy, adjuvant or neoadjuvant chemotherapy, or idiopathic thrombocytopenia purpura.

In some embodiments, the adjuvant or neoadjuvant chemotherapy comprises at least one of docetaxel and cyclophosphamide. In some embodiments, the adjuvant or neoadjuvant chemotherapy comprises a combination of docetaxel and cyclophosphamide.

In other embodiments, the therapeutic effective amount is a unit dosage form selected from: 12.5 µg/kg, 25 µg/kg, 50 µg/kg, 100 µg/kg, and 200 µg/kg. In some embodiments, the patient's weight ranges from 30 kg to 180 kg. In some embodiments, the EFLAPEGRASTIM administered at a fixed dose of 13.2 mg regardless of patient's weight.

In other embodiments, the therapeutic effective amount is a fixed dose repeated 1 to 3 days post chemotherapy, radiation or adjuvant or neoadjuvant therapy.

In some embodiments, the fixed dose is 13.2 mg. In some embodiments, the fixed dose is provided in a dosage volume of about 0.4 ml to about 1 ml. In some embodiments, the fixed dose is provided in a dosage volume of about 0.6 ml.

In certain embodiments, the protein complex is EFLA-PEGRASTIM administered at doses of 13.2 mg/0.6 mL (containing 3.6 mg rhG-CSF). In other embodiments, the present methodology, further includes administering to the patient a therapeutically effective amount of a second agent, such as an anti-cancer agent.

In some embodiments, the immunoglobulin Fc region comprises a polypeptide sequence of SEQ ID NO: 1. In some embodiments, the modified G-CSF comprises a polypeptide sequence of SEQ ID NO: 2.

Fc region. In some embodiments, both ends of the non-peptidyl polymer are respectively linked to the physiologically active polypeptide and the immunoglobulin Fc region through reactive groups by a covalent bond. In a preferred embodiment, the immunoglobulin Fc region is aglycosylated.

In some embodiments, the G-CSF complex composition is administered to the patient within about 5 hours, 2 hours, 1 hour, or half an hour of the completion of chemotherapy. In other embodiments, the composition is administered 1-3 days after the completion of the chemotherapy regime in each cycle. In other embodiments, the composition is administered about 24 hours after the completion of the chemotherapy regime in each cycle. In some embodiments, the composition is administered before the chemotherapy, e.g., 5 days, 4 days, 2 days, 1 day, 20 hours, 15 hours, 10 hours, 5 hours, 3 hours, 1 hour before the chemotherapy.

Non-limiting examples of the chemotherapy include alkylating agents: Busulfan, dacarbazine, ifosfamide, hexamethylmelamine, thiotepa, dacarbazine, lomustine, chlorambucil, procarbazine, altretamine, estramustine phosphate, mechlorethamine, streptozocin, temozolomide, Semustine cyclophosphamide; platinum agents: spiroplatin, tetraplatin,

| SEQ ID NO | SEQUENCE | OTHER INFORMATION |
|---|---|---|
| SEQ ID NO: 1 | TPLGPASSLPQSFLLKSLEQVRKIQGDGAALQEK LCATYKLCHPEELVLLGHSLGIPWAPLSSCSSQA LQLAGCLSQLHSGLFLYQGLLQALEGISPELGPTL DTLQLDVADFATTIWQQMEELGMAPALQPTQG AMPAFASAFQRRAGGVLVASHLQSFLEVSYRVL RHLAQP | G-CSF (17Ser and 65 Ser) |
| SEQ ID NO: 2 | PSCPAPEFLGGPSVFLFPPKPKDTLMISRTPEVTC VVVDVSQEDPEVQFNWYVDGVEVHNAKTKPRE EQFNSTYRVVSVLTVLHQDWLNGKEYKCKVSN KGLPSSIEKTISKAKGQPREPQVYTLPPSQEEMTK NQVSLTCLVKGFYPSDIAVEWESNGQPENNYKT TPPVLDSDGSFFLYSRLTVDKSRWQEGNVFSCSV MHEALHNHYTQKSLSLSLGK | Immunoglobulin Fc region (IgG4) |

In some embodiments, the protein complex employed in the present methods contain (a) each domain of the immunoglobulin Fc fragment is a hybrid of domains, in which each domain has a different origin derived from immunoglobulins selected from the group consisting of IgG, IgA, IgD, IgE, and IgM; (b) the immunoglobulin Fc fragment is a dimer or multimer consisting of single chain immunoglobulins comprising domains having the same origin; (c) the immunoglobulin Fc fragment is an IgG4 Fc fragment; or (d) the immunoglobulin Fc fragment is a human aglycosylated IgG4 Fc fragment.

In certain embodiments, the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof. In a preferred embodiment, the non-peptidyl polymer is polyethylene glycol.

In another aspect, the present disclosure provides a method for treating or preventing neutropenia in a patient receiving chemotherapy. The method comprises administering to said patient a protein complex comprising a modified G-CSF linked to an immunoglobulin Fc region via a non-peptidyl polymer, wherein the non-peptidyl polymer is site-specifically linked to an N-terminus of the immunoglobulin ormaplatin, iproplatin, ZD-0473 (AnorMED), oxaliplatin carboplatin, lobaplatin (Aeterna), satraplatin (Johnson Matthey), BBR-3464 (Hoffmann-La Roche), SM-11355 (Sumitomo), AP-5280 (Access), cisplatin, arboplatin, cisplatin, satraplatin, oxaliplatin, nedaplatin, triplatin tetranitrate, temozolomide, procarbazin; antimetabolites: azacytidine, Floxuridine, 2-chlorodeoxyadenosine, 6-mercaptopurine, 6-thioguanine, cytarabine, 2-fluorodeoxy cytidine, methotrexate, tomudex, fludarabine, raltitrexed, trimetrexate, deoxycoformycin, pentostatin, hydroxyurea, decitabine (SuperGen), clofarabine (Bioenvision), irofulven (MGI Pharma), DMDC (Hoffmann-La Roche), ethynylcytidine (Taiho), gemcitabine, capecitabine; topoisomerase inhibitors: amsacrine, epirubicin, etoposide, teniposide or mitoxantrone, 7-ethyl-10-hydroxy-camptothecin, dexrazoxanet (TopoTarget), pixantrone (Novuspharma), rebeccamycin analogue (Exelixis), BBR-3576 (Novuspharma), rubitecan (SuperGen), irinotecan (CPT-11), topotecan; antitumor antibiotics: valrubicin, therarubicin, idarubicin, rubidazone, plicamycin, porfiromycin mitoxantrone (novantrone), amonafide, azonafide, anthrapyrazole, oxantrazole, losoxantrone, MEN-10755 (Menarini), GPX-100 (Gem Pharmaceuticals), Epirubicin, mitoxantrone, doxorubicin; antimitotic agents: colchicine, vinblastine, vindesine, dolastatin 10 (NCI), rhizoxin (Fujisawa), mivobulin (Warner-Lambert), cemadotin (BASF), RPR 109881A (Aventis), TXD 258 (Aventis), epothilone B (Novartis), T 900607 (Tularik), T 138067 (Tularik), cryptophycin 52 (Eli Lilly), vinflunine (Fabre), auristatin PE (Teikoku Hormone), BMS 247550 (BMS), BMS 184476 (BMS), BMS 188797 (BMS), taxoprexin (Protarga), SB 408075 (GlaxoSmithKline), Vinorelbine, Trichostatin A, E7010 (Abbott), PG-TXL (Cell Therapeutics), IDN 5109 (Bayer), A 105972 (Abbott), A 204197 (Abbott), LU 223651 (BASF), D 24851 (ASTAMedica), ER-86526 (Eisai), combretastatin A4 (BMS), isohomohalichondrin-B (PharmaMar), ZD 6126 (AstraZeneca), AZ10992 (Asahi), IDN-5109 (Indena), AVLB (Prescient NeuroPharma), azaepothilone B (BMS), BNP-7787 (BioNumerik), CA-4 prodrug (OXiGENE), dolastatin-10 (NIH), CA-4 (OXiGENE), docetaxel, vincristine, paclitaxel; aromatase inhibitors: aminoglutethimide, atamestane (BioMedicines), letrozole, anastrazole, YM-511 (Yamanouchi), formestane, exemestane; thymidylate synthase inhibitors: pemetrexed (Eli Lilly), ZD-9331 (BTG), nolatrexed (Eximias), CoFactor™ (BioKeys); dna antagonists: trabectedin (PharmaMar); glufosfamide (Baxter International), albumin+32P (Isotope Solutions), thymectacin (NewBiotics), edotreotide (Novartis), mafosfamide (Baxter International), apaziquone (Spectrum Pharmaceuticals), 06 benzyl guanine (Paligent); farnesyltransferase inhibitors: arglabin (NuOncology Labs), lonafarnib (Schering-Plough), BAY-43-9006 (Bayer), tipifarnib (Johnson & Johnson), perillyl alcohol (DOR BioPharma); pump inhibitors: CBT-1 (CBA Pharma), tariquidar (Xenova), MS-209 (Schering AG), zosuquidar trihydrochloride (Eli Lilly), biricodar dicitrate (Vertex); histone acetyltransferase inhibitors: tacedinaline (Pfizer), SAHA (Aton Pharma), MS-275 (Schering AG), pivaloyloxymethyl butyrate (Titan), depsipeptide (Fujisawa); metalloproteinase inhibitors: Neovastat (Aeterna Laboratories), marimastat (British Biotech), CMT-3 (CollaGenex), BMS-275291 (Celltech); ribonucleoside reductase inhibitors: gallium maltolate (Titan), triapine (Vion), tezacitabine (Aventis), didox (Molecules for Health); tnf alpha agonists/antagonists: virulizin (Lorus Therapeutics), CDC-394 (Celgene), revimid (Celgene); endothelin a receptor antagonist: atrasentan (Abbott), ZD-4054 (AstraZeneca), YM-598 (Yamanouchi); retinoic acid receptor agonists: fenretinide (Johnson & Johnson), LGD-1550 (Ligand), alitretinoin (Ligand); immuno-modulators: Pembrolizumab (formerly lambrolizumab, brand name Keytruda); interferon, oncophage (Antigenics), GMK (Progenics), adenocarcinoma, vaccine (Biomira), CTP-37 (AVI BioPharma), IRX-2 (Immuno-Rx), PEP-005 (Peplin Biotech), synchrovax vaccines (CTL Immuno), melanoma vaccine (CTL Immuno), p21 RAS vaccine (GemVax), MAGE-A3 (GSK), nivolumab (BMS), abatacept (BMS), dexosome therapy (Anosys), pentrix (Australian Cancer Technology), ISF-154 (Tragen), cancer vaccine (Intercell), norelin (Biostar), BLP-25 (Biomira), MGV (Progenics), ß-alethine (Dovetail), CLL therapy (Vasogen), Ipilimumab (BMS), CM-10 (cCam Biotherapeutics), MPDL3280A (Genentech); hormonal and antihormonal agents: estrogens, conjugated estrogens, ethinyl estradiol, chlortrianisen, idenestrol, hydroxyprogesterone caproate, medroxyprogesterone, testosterone, testosterone propionate, fluoxymesterone, methyltestosterone, diethylstilbestrol, megestrol, bicalutamide, flutamide, nilutamide, dexamethasone, prednisone, methylprednisolone, prednisolone, aminoglutethimide, leuprolide, octreotide, mitotane, P-04 (Novogen), 2-methoxyestradiol (EntreMed), arzoxifene (Eli Lilly), tamoxifen, toremofine, goserelin, Leuporelin, bicalutamide; photodynamic agents: talaporfin (Light Sciences), Theralux (Theratechnologies), motexafin gadolinium (Pharmacyclics), Pd-bacteriopheophorbide (Yeda), lutetium texaphyrin (Pharmacyclics), hypericin; and kinase inhibitors: afatinib, osimertinib, poziotinib (Spectrum), imatinib (Novartis), leflunomide (Sugen/Pharmacia), ZD1839 (AstraZeneca), erlotinib (Oncogene Science), canertinib (Pfizer), squalamine (Genaera), SU5416 (Pharmacia), SU6668 (Pharmacia), ZD4190 (AstraZeneca), ZD6474 (AstraZeneca), vatalanib (Novartis), PKI166 (Novartis), GW2016 (GlaxoSmithKline), EKB-509 (Wyeth), trastuzumab (Genentech), OSI-774 (Tarceva™), CI-1033 (Pfizer), SU11248 (Pharmacia), RH3 (York Medical), Genistein, Radicinol, Met-MAb (Roche), EKB-569 (Wyeth), kahalide F (PharmaMar), CEP-701 (Cephalon), CEP-751 (Cephalon), MLN518 (Millenium), PKC412 (Novartis), Phenoxodiol (Novogen), C225 (ImClone), rhu-Mab (Genentech), MDX-H210 (Medarex), 2C4 (Genentech), MDX-447 (Medarex), ABX-EGF (Abgenix), IMC-1C11 (ImClone), Tyrphostins, Gefitinib (Iressa), PTK787 (Novartis), EMD 72000 (Merck), Emodin, Radicinol, Vemurafenib (B-Raf enzyme inhibitor, Daiichi Sankyo), SR-27897 (CCK A inhibitor, Sanofi-Synthelabo), tocladesine (cyclic AMP agonist, Ribapharm), alvocidib (CDK inhibitor, Aventis), CV-247 (COX-2 inhibitor, Ivy Medical), P54 (COX-2 inhibitor, Phytopharm), CapCell™ (CYP450 stimulant, Bavarian Nordic), GCS-100 (ga13 antagonist, GlycoGenesys), G17DT immunogen (gastrin inhibitor, Aphton), efaproxiral (oxygenator, Allos Therapeutics), PI-88 (heparanase inhibitor, Progen), tesmilifene (histamine antagonist, YM BioSciences), histamine (histamine H2 receptor agonist, Maxim), tiazofurin (IMPDH inhibitor, Ribapharm), cilengitide (integrin antagonist, Merck KGaA), SR-31747 (IL-1 antagonist, Sanofi-Synthelabo), CCI-779 (mTOR kinase inhibitor, Wyeth), exisulind (PDE V inhibitor, Cell Pathways), CP-461 (PDE V inhibitor, Cell Pathways), AG-2037 (GART inhibitor, Pfizer), WX-UK1 (plasminogen activator inhibitor, Wilex), PBI-1402 (PMN stimulant, ProMetic LifeSciences), bortezomib (proteasome inhibitor, Millennium), SRL-172 (T cell stimulant, SR Pharma), TLK-286 (glutathione S transferase inhibitor, Telik), PT-100 (growth factor agonist, Point Therapeutics), midostaurin (PKC inhibitor, Novartis), bryostatin-1 (PKC stimulant, GPC Biotech), CDA-II (apoptosis promotor, Everlife), SDX-101 (apoptosis promotor, Salmedix), rituximab (CD20 antibody, Genentech, carmustine, Mitoxantrone, Bleomycin, Absinthin, Chrysophanic acid, Cesium oxides, BRAF inhibitors, PDL1 inhibitors, MEK inhibitors, bevacizumab, angiogenesis inhibitors, dabrafenib, ceflatonin (apoptosis promotor, ChemGenex); BCX-1777 (PNP inhibitor, BioCryst), ranpirnase (ribonuclease stimulant, Alfacell), galarubicin (RNA synthesis inhibitor, Dong-A), tirapazamine (reducing agent, SRI International), N, acetylcysteine (reducing agent, Zambon), R-flurbiprofen (NF-kappaB inhibitor, Encore), 3CPA (NF-kappaB inhibitor, Active Biotech), seocalcitol (vitamin D receptor agonist, Leo), 131-I-TM-601 (DNA antagonist, TransMolecular), eflornithine (ODC inhibitor, *ILEX* Oncology), minodronic acid (osteoclast inhibitor, Yamanouchi), indisulam (p53 stimulant, Eisai), aplidine (PPT inhibitor, PharmaMar), gemtuzumab (CD33 antibody, Wyeth Ayerst), PG2 (hematopoiesis enhancer, Pharmagenesis), Immunol™ (triclosan oral rinse, Endo), triacetyluridine (uridine prodrug, Wellstat), SN-4071 (sarcoma agent, Signature BioScience), TransMID-107$^{Tm}$ (immunotoxin, KS Biomedix), PCK-3145 (apoptosis promotor, *Procyon*), doranidazole (apoptosis promotor, Pola), CHS-828 (cytotoxic agent, Leo), trans-retinoic acid (differentiator, NIH), MX6 (apoptosis promotor, MAXIA), apomine (apoptosis promotor, *ILEX* Oncology), urocidin (apoptosis promotor, Bioniche), Ro-31-7453 (apoptosis promotor, La Roche), brostallicin (apoptosis promotor, Pharmacia), β-lapachone, gelonin, cafestol, kahweol, caffeic acid, Tyrphostin AG, PD-1 inhibitors, CTLA-4 inhibitors, sorafenib, BRAF inhibitors, mTOR inhibitors (e.g. Vistusertib, everolimus/Afinitor, rapamycin, dactolisib, BGT226, SF1126, PKI-587, NVPBE235) and Pan-HER inhibitor (e.g. afatinib, neratinb, AC480).

Non-limiting examples of tyrosine kinase inhibitors as chemotherapy include erlotinib, gefitinib, afatinib, dacomitinib, and osimertinib.

In some embodiments, the agent for chemotherapy is selected from bevacizurnab, bortezomib, capecitabine, cetuximab, fluorouracil, imatinib, irinotecan, leucovorin, oxaliplatin, panitumumab, pemetrexed, temozolomide, cisplatin, paclitaxel, erlotinib, sunitinib, lapatinib, sorafenib, carboplatin, doxorubicin, docetaxel, gemcitabine, etoposide, gefitinib, PD153035, cetuximab, bevacizumab, panitumumab, trastuzumab, anti-c-Met antibodies, gefitinib, ZD6474, EMD-72000, pariitumab, ICR-62, CI-1033, lapatinib, AEE788, EKB-569, EXEL 7647/EXEL 0999, erlotinib, imatinib, sorafinib, sunitinib, dasatinib, vandetinib, temsirolimus, PTK787, pazopanib, AZD2171, everolimus, seliciclib, AMG 706, axitinib, PD0325901, PKC-412, CEP701, XL880, bosutinib, BIBF1120, BIBF1120, nilotinib, AZD6244, HKI-272, MS-275, BI2536, GX15-070, AZD0530, enzastaurin, MLN-518, ARQ197, CM101, IFN-.alpha., IL-12, platelet factor-4, suramin, SU5416, thrombospondin, VEGFR antagonists, angiostatic steroids plus heparin, Cartilage-Derived Angiogenesis Inhibitory Factor, matrix metalloproteinase inhibitors, batimastat, marimastat, angiostatin, endostatin, 2-methoxyestradiol, tecogalan, thrombospondin, .alpha.V.beta.3 inhibitors, linomide, and ADH-1, chlorambucil, cyclophosphamide, ifosfamide, mechlorethamine, melphalan, uracil mustard, thiotepa, busulfan, carmustine, lomustine, streptozocin, carboplatin, cisplatin, satraplatin, oxaliplatin, altretamine, ET-743, XL119, dacarbazine, chlormethine, bendamustine, trofosfamide, uramustine, fotemustine, nimustine, prednimustine, ranimustine, semustine, nedaplatin, triplatin tetranitrate, mannosulfan, treosulfan, temozolomide, carboquone, triaziquone, triethylenemelamine, procarbazin, doxorubicin, daunorubicin, epirubicin, idarubicin, anthracenedione, mitoxantrone, mitomycin C, bleomycin, dactinomycin, plicatomycin, irinotecan, camptothecin, rubitecan, belotecan, etoposide, teniposide, topotecan, paclitaxel, taxol, docetaxel, BMS-275183, xyotax, tocosal, vinorlebine, vincristine, vinblastine, vindesine, vinzolidine, etoposide, teniposide, ixabepilone, larotaxel, ortataxel, tesetaxel, ispinesib, fluorouracil, floxuridine, methotrexate, xeloda, arranon, leucovorin, hydroxyurea, thioguanine, mercaptopurine, cytarabine, pentostatin, fludarabine phosphate, cladribine, asparaginase, gemcitabine, pemetrexed, bortezomib, aminopterin, raltitrexed, clofarabine, enocitabine, sapacitabine, azacitidine.

Further examples of agent for chemotherapy include SHP2 inhibitors (e.g., RMC-4550 and RMC-4630), phosphatase inhibitors (e.g., Tautomycin), CDK 4/6 inhibitors (abemaciclib (Lilly), palbociclib (Pfizer)), protein-protein interaction disruptors (BI 1701963), HSP90 inhibitor, tubulin inhibitor, apoptosis inhibitor, chemopreventative agent, and therapies targeting PBK/AKT/mTOR pathway.

In some embodiments of the methods disclosed herein, the subject has not previously received a systemic treatment (e.g., chemotherapy, radiotherapy, gene therapy, surgery, hormonal therapy, anti-angiogenic therapy or immunotherapy) for the cancer. In some embodiments, the subject has previously received at least one, at least two, at least three, at least four, at least five, at least six, at least seven or more lines of therapy for the cancer.

In some embodiment, the present invention provides the protein complex in which the immunoglobulin Fc region comprises one of CH2, CH3, and CH4 domains. For example, the immunoglobulin Fc region can include CH2 and CH3 domains. In some embodiments, the immunoglobulin Fc region further includes a hinge region.

In some embodiments, the immunoglobulin Fc region is an immunoglobulin Fc fragment derived from IgG, IgA, IgD, IgE, or IgM. In some embodiments, each domain of the immunoglobulin Fc fragment is a hybrid of domains and each domain has a different origin derived from immunoglobulins selected from the group consisting of IgG, IgA, IgD, IgE, and IgM. In some embodiments, the immunoglobulin Fc fragment is a dimer or multimer consisting of single chain immunoglobulins comprising domains having the same origin. In some embodiments, the immunoglobulin Fc fragment is an IgG4 Fc fragment.

In some embodiments, the non-peptidyl polymer can be one of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, preferably the non-peptidyl polymer is polyethylene glycol. In some embodiments, the non-peptidyl polymer is 3.4 kDa polyethylene glycol.

In some embodiments, the reactive group of the non-peptidyl polymer can be one of an aldehyde group, a maleimide group, and a succinimide derivative. The aldehyde group can be a propionaldehyde group or a butyraldehyde group. The succinimide derivative can be succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In some embodiments, the non-peptidyl polymer has an aldehyde group as a reactive group at both ends. In some embodiments, the non-peptidyl polymer has an aldehyde group and a maleimide group as a reactive group at both ends, respectively. In some embodiments, the non-peptidyl polymer has an aldehyde group and a succinimide group as a reactive group at both ends, respectively.

In some embodiments, the present invention provides the protein complex in which each end of the non-peptidyl polymer is linked to the N-terminus of the immunoglobulin Fc region; and the N-terminus, C-terminus, or a free reactive group of a lysine residue, a histidine residue, or a cysteine residue of the physiologically active polypeptide, respectively.

In another aspect, this disclosure provides a method for treating or preventing neutropenia in a patient receiving chemotherapy. The method comprises comprising administering to said patient a protein complex comprising a physiologically active polypeptide linked to an immunoglobulin Fc region via a non-peptidyl polymer, wherein the non-peptidyl polymer is site-specifically linked to an N-terminus of the immunoglobulin Fc region.

In some embodiments, the physiologically active polypeptide can be one of a hormone, a cytokine, an enzyme, an antibody, a growth factor, a transcription factor, a blood coagulation factor, a vaccine, a structural protein, a ligand protein, and a receptor. In some embodiments, the physiologically active polypeptide is G-CSF.

In another aspect, this disclosure provides a pharmaceutical composition for improving in vivo duration and stability of the physiologically active polypeptide comprising the protein complex as an active ingredient.

A specific embodiment of the present invention provides a composition comprising the protein complex in an amount of 90% or higher.

In another aspect, this disclosure provides a pharmaceutical container containing the preparation for delivery of the present composition. Exemplary pharmaceutical containers include an injector, a syringe, vial, infusion bottle, ampoule or carpoule, for example, a syringe equipped with a needle protection system or a carpoule within an injection pen. According to one embodiment, the present invention provides an injector that includes a container having a wall with an interior surface and a seal assembly with an interior surface, the interior surfaces of the wall and the seal assembly defining a closed sterile reservoir filled with a drug product.

The injector may also include a fluid delivery system comprising a clean, unsheathed, rigid container needle having a point disposed only partially through the seal assembly in a storage state, and disposed through the interior surface of the seal assembly into the sterile reservoir in a delivery state. Further, the injection may include an actuator that is adapted to move the container needle from the storage state to the delivery state. In one embodiment, the wall of the container may be a rigid wall or a flexible wall, and the seal assembly may be a flexible unitary wall having an interior surface that defines the interior surface of the seal assembly. The flexible unitary wall may define a septum disposed across the opening and fixedly attached to the wall of the container.

Alternatively, the wall of the container may define a bore, and the unitary flexible wall may define a stopper that is moveable along the bore. In such a case, the wall of the container may define a closed end opposite the stopper and an open end in which the stopper is disposed. As a further alternative, the wall of the container may define a bore with an opening in fluid communication with a first end of the bore, and the unitary flexible wall defines a septum disposed across the opening and fixedly attached to the wall of the container, the container further comprising a stopper that is disposed within a second end of the bore and is moveable along the bore.

Still another aspect of the present invention provides for the use of the instant composition as set forth above in treatment relating to bone marrow transplantation. The method comprises administering therapeutically effective doses to patients in need in connection with bone marrow transplantation and mobilization of stem cells.

In another aspect, this disclosure provides a method of prophylactically treating chemotherapy induced neutropenia caused by administering a docetaxel and cyclophosphamide regimen with fixed doses of EFLAPEGRASTIM 3.6 mg G-CSF, about 24 hours after the last dose of docetaxel and cyclophosphamide chemotherapy.

In some embodiments, the method comprises administering to the patient a therapeutically effective amount of a second agent, such as antitumor/anticancer agents, including chemotherapeutic agents and immunotherapeutic agents.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, methyldopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, xeloda, gemcitabine, KRAS mutation covalent inhibitors and goserelin; and pharmaceutically acceptable salts, acids or derivatives of any of the above. Additional examples include irinotecan, oxaliplatinum, and other standard colon cancer regimens.

An "immunotherapeutic agent" is a biological agent useful in the treatment of cancer. Examples of immunotherapeutic agents include atezolizumab, avelumab, blinatumomab, daratumumab, cemiplimab, durvalumab, elotuzumab, laherparepvec, ipilimumab, nivolumab, obinutuzumab, ofatumumab, pembrolizumab, cetuximab, and talimogene.

Protein Complexes and Pharmaceutical Compositions

As used herein, the term "protein complex" or "complex" refers to a structure in which at least one physiologically active polypeptide, at least one non-peptidyl polymer having a reactive group at both ends thereof, and at least one immunoglobulin Fc region are linked to each other via a covalent bond. Further, a structure in which only two molecules selected from the physiologically active polypeptide, the non-peptidyl polymer, and the immunoglobulin Fc region are linked to each other via a covalent bond is called "conjugate" in order to distinguish it from the "complex."

The protein complex of the present invention may be a protein complex in which the PEG is linked to the modified G-CSF and the immunoglobulin Fc region through reactive groups at both ends thereof by a covalent bond, respectively.

As used herein, the term "physiologically active polypeptide," "physiologically active protein," "active protein," or "protein drug" refers to a polypeptide or a protein having some kind of antagonistic activity to a physiological event in vivo, and these terms may be used interchangeably.

As used herein, pharmacokinetics parameters described herein have the same meaning understood in the art, including maximum serum concentration ($C_{max}$), time of maximum concentration ($T_{max}$), area under the serum concentration-time curve to the last measured concentration ($AUC_{last}$) and to infinity (AUC), apparent total body clearance (CL/F), terminal elimination half-life ($t_{1/2}$), and mean residence time ($MRT_{last}$).

As used herein, the term "non-peptidyl polymer" refers to a biocompatible polymer including two or more repeating units which are linked to each other by any covalent bond excluding a peptide bond, but is not limited thereto.

As used herein, the term "immunoglobulin Fc region" refers to a region of an immunoglobulin molecule, except for the variable regions of the heavy and light chains, the heavy-chain constant region 1 (CH1) and the light chain constant region 1 (CL1) of an immunoglobulin. The immunoglobulin Fc region may further include a hinge region at the heavy-chain constant region. In particular, the immunoglobulin Fc region of the present invention may be a fragment including a part or all of the Fc region, and in the present invention, the immunoglobulin Fc region may be used interchangeably with an immunoglobulin fragment.

A native Fc has a sugar chain at position Asn297 of heavy-chain constant region 1, but E. coli-derived recombinant Fc is expressed as an aglycosylated form. The removal of sugar chains from Fc results in a decrease in binding affinity of Fc gamma receptors 1, 2, and 3 and complement (c1q) to heavy-chain constant region 1, leading to a decrease or loss in antibody-dependent cell-mediated cytotoxicity or complement-dependent cytotoxicity.

As used herein, the term "immunoglobulin constant region" may refer to an Fc fragment including heavy-chain constant region 2 (CH2) and heavy-chain constant region 3 (CH3) (or containing heavy-chain constant region 4 (CH4)), except for the variable regions of the heavy and light chains, the heavy-chain constant region 1 (CHI) and the light chain constant region (CL) of an immunoglobulin, and may further include a hinge region at the heavy chain constant region. Further, the immunoglobulin constant region of the present invention may be an extended immunoglobulin constant region including a part or all of the Fc region including the heavy-chain constant region 1 (CH1) and/or the light chain constant region (CL), except for the variable regions of the heavy and light chains of an immunoglobulin, as long as it has a physiological function substantially similar to or better than the native protein.

Meanwhile, the immunoglobulin constant region may originate from humans or animals, such as cows, goats, pigs, mice, rabbits, hamsters, rats, guinea pigs, etc., and may preferably be of human origin. In addition, the immunoglobulin constant region may be selected from constant regions derived from IgG, IgA, IgD, IgE, IgM, or combinations or hybrids thereof, preferably, derived from IgG or IgM, which are the most abundant thereof in human blood, and most preferably, derived from IgG, which is known to improve the half-life of ligand-binding proteins. In the present invention, the immunoglobulin Fc region may be a dimer or multimer consisting of single-chain immunoglobulins of domains of the same origin.

As used herein, the term "combination" means that polypeptides encoding single-chain immunoglobulin constant regions (preferably Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single-chain of an immunoglobulin constant region (preferably, an Fc region). In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof. Preferred are the IgG2 and IgG4 subclasses, and most preferred is the Fc region of IgG4 rarely having effector functions such as complement dependent cytotoxicity (CDC).

The immunoglobulin constant region may have the glycosylated form to the same extent as, or to a greater or lesser extent than the native form or may be the deglycosylated form. Increased or decreased glycosylation or deglycosylation of the immunoglobulin constant region may be achieved by typical methods, for example, by using a chemical method, an enzymatic method or a genetic engineering method using microorganisms. Herein, when deglycosylated, the complement (C1q) binding to an immunoglobulin constant region becomes significantly decreased, and antibody-dependent cytotoxicity or complement-dependent cytotoxicity is reduced or removed, thereby not inducing unnecessary immune responses in vivo. In this context, deglycosylated or aglycosylated immunoglobulin constant regions are more consistent with the purpose of drug carriers. Accordingly, the immunoglobulin Fc region may be more specifically an aglycosylated Fc region derived from human IgG4, that is, a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., C1q fixation sites, or ADCC sites, may be eliminated to remove the effector function. The techniques of preparing the sequence derivatives of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, AlaJGly, Ala/Thr, Ser/Asn, Ala/Val, Ser/Gly, Thr/Phe, Ala/Pro, Lys/Arg, Asp/Asn, Leu/Ile, LeuNal, Ala/Glu, and Asp/Gly, in both directions. Optionally, amino acids may be modified by phosphorylation, sulfation, acrylation, glycosylation, methylation, farnesylation, acetylation, amidation, or the like.

The above-described immunoglobulin constant region derivative may be a derivative which has a biological activity equivalent to that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c.

Preferably, a human-derived immunoglobulin constant region may be a recombinant immunoglobulin constant region that is obtained from a microorganism.

The protein complex of the present invention may include one or more of a unit structure of a [physiologically active polypeptide/non-peptidyl polymer/immunoglobulin Fc region], in which all components may be linked in a linear form by a covalent bond. The non-peptidyl polymer may have a reactive group at both ends thereof and is linked to the physiologically active polypeptide and the immunoglobulin Fc region through the reactive group by a covalent bond, respectively. That is, at least one conjugate of the physiologically active polypeptide and the non-peptidyl polymer is linked to one immunoglobulin Fc region by a covalent bond, thereby forming a monomer, dimer, or multimer of the physiologically active polypeptide, which is mediated by the immunoglobulin Fc region. Therefore, an increase in vivo activity and stability may be more effectively achieved.

The reactive group at both ends of the non-peptidyl polymer is preferably selected from the group consisting of a reactive aldehyde group, a propionaldehyde group, a butyraldehyde group, a maleimide group, and a succinimide derivative. The succinimide derivative may be hydroxy succinimidyl, succinimidyl carboxymethyl, succinimidyl valerate, succinimidyl methyl butanoate, succinimidyl methyl propionate, succinimidyl butanoate, succinimidyl propionate, N-hydroxysuccinimide, or succinimidyl carbonate. In particular, when the non-peptidyl polymer has a reactive aldehyde group at both ends, it is effective in linking both of the ends with the physiologically active polypeptide and the immunoglobulin with minimal non-specific reactions. A final product generated by reductive alkylation by an aldehyde bond is much more stable than when linked by an amide bond.

The reactive groups at both ends of the non-peptidyl polymer of the present invention may be the same as or different from each other. The non-peptide polymer may possess aldehyde reactive groups at both ends, or it may possess an aldehyde group at one end and a maleimide reactive group at the other end, or an aldehyde group at one end and a succinimide reactive group at the other end, but is not limited thereto.

For example, the non-peptide polymer may possess a maleimide group at one end and an aldehyde group, a propionaldehyde group, or a butyraldehyde group at the other end. Also, the non-peptide polymer may possess a succinimidyl group at one end and a propionaldehyde group, or a butyraldehyde group at the other end. When a polyethylene glycol having a reactive hydroxy group at both ends thereof is used as the non-peptidyl polymer, the hydroxy group may be activated to various reactive groups by known chemical reactions, or a commercially available polyethylene glycol having a modified reactive group may be used so as to prepare the protein complex of the present invention.

When the physiologically active polypeptide and the immunoglobulin Fc region are linked via the non-peptidyl polymer, each of both of the ends of the non-peptidyl polymer may bind to the N-terminus of the immunoglobulin Fc region and the N-terminus (amino terminus), C-terminus (carboxy terminus), or free reactive group of a lysine residue, a histidine residue, or a cysteine residue of the physiologically active polypeptide.

As used herein, the term "N-terminus" refers to an N-terminus of a peptide, which is a site to which a linker including a non-peptidyl polymer can be conjugated for the purpose of the present invention. Examples of the N-terminus may include not only amino acid residues at the distal end of the N-terminus, but hut also amino acid residues near the N-terminus, but are not limited thereto. Specifically, the 1st to the 20th amino acid residues from the distal end may be included.

The non-peptidyl polymer of the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof, and specifically, polyethylene glycol, but is not limited thereto. Also, derivatives thereof well known in the art and easily prepared within the skill of the art are included in the non-peptidyl polymer of the present invention. The non-peptidyl polymer may have a molecular weight in the range of 1 kDa to 100 kDa, and specifically 1 kDa to 20 kDa.

The physiologically active polypeptide of the present invention may be exemplified by various physiologically active polypeptides such as hormones, cytokines, interleukins, interleukin-binding proteins, enzymes, antibodies, growth factors, transcription factors, blood factors, vaccines, structural proteins, ligand proteins or receptors, cell surface antigens, receptor antagonists, and derivatives or analogs thereof.

Specifically, the physiologically active polypeptide includes human growth hormones, growth hormone-releasing hormones, growth hormone-releasing peptides, interferons and interferon receptors (e.g., interferon-alpha, -beta, and -gamma, soluble type I interferon receptors), colony-stimulating factors, interleukins (e.g., interleukin-1, -2, -3, -4, -6, -7, -8, -9, -10, -11, -12, -13, -14, -15, -16, -17, -18, -19, -20, -21, -22, -23, -24, -25, -26, -27, -28, -29, -30. Etc.), and interleukin receptors (e.g; IL-1 receptor. IL-4 receptor, etc.), enzymes (e.g., glucocerebrosidase, iduronate-2-sulfatase, alpha-galactosidase-A, agalsidase alpha,beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- and cytokine-binding proteins (e.g., IL-18 bp, TNF-binding protein, etc.), macrophage-activating factors, macrophage peptides, B-cell factors, T-cell factors, protein A, allergy inhibitors, cell necrosis glycoproteins, immunotoxins, lymphotoxins, tumor necrosis factor, tumor suppressors, transforming growth factor, alpha-1 anti-trypsin, albumin, alpha-lactalbumin, apolipoprotein-E, erythropoietin, glycosylated crythropoictin, angiopoietins, hemoglobin, thrombin, thrombin receptors activating peptides, throm-bomodulin, blood factors VII, VIIa, VIII, IX, and XIII, plasminogen activators, fibrin-binding peptides, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone-stimulating protein, calcitonin, insulin, oxyntomodulin, glucagon, glucagon derivatives, glucagon-like peptides, exendins (Exendin4), atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors (e.g., nerve growth factor, cilliary neurotrophic factor, axogenesis factor-1, brain-natriuretic peptide, glial-derived neu-rotrophic factor, netrin, neutrophil inhibitor factor, neurotrophic factor, neurturin, etc.), parathyroid hormone, relaxin, secretin, somatomedin, insulin-like growth factor, adrenocortical hormone, glucagon, cholecystokinin, pancreatic polypeptide, gastrin-releasing peptide, corticotrophin-releasing factor, thyroid-stimulating hormone, autotaxin, lactoferrin, myostatin, receptors (e.g., TNFR (P75), TNFR (P55), IL-1 receptor, VEGF receptor, B-cell-activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2, and Fd), and virus-derived vaccine antigens.

Specifically, the physiologically active polypeptide of the present invention is a granulocyte colony-stimulating factor. In the preferred embodiment, the polypeptide is G-CSF.

In the present invention, the antibody fragment may be Fab, Fab', F(ab'), Fd, or scFv having an ability to bind to a specific antigen, and preferably, Fab.' The Fab fragments include the variable domain (VL) and constant domain (CL) of the light chain and the variable domain (VH) and the first constant domain (CH1) of the heavy chain. The Fab' fragments differ from the Fab fragments in terms of the addition of several amino acid residues including one or more cysteine residues from the hinge region at the carboxyl terminus of the CH1 domain. The Fd fragments are fragments consisting of only the VH and CH1 domains, and the F(ab')2 fragments are produced by binding of two molecules of Fab' fragments by either disulfide bonding or a chemical reaction. The scFv fragment is a single polypeptide chain, in which only VL and VH domains are linked to each other by a peptide linker Further, the protein complex of the present invention may be used in the development of long-acting protein formulations of animal growth hormone such as bovine growth hormone or porcine growth hormone, and long-acting protein formulations for treatment or prevention of animal disease, such as interferon.

Another aspect of the present invention provides a method of preparing the protein complex of the present invention. In particular, the present invention provides a method of preparing a position-specific protein complex, the method comprising: (a) preparing a protein complex by linking least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

The immunoglobulin Fc region of the present invention may be in the form of a dimer, or in the form of a homodimer or heterodimer. Therefore, the immunoglobulin Fc region constituting the protein complex of the present invention may include one or two or more of an N-terminus. Thus, the immunoglobulin Fc region may be linked to at least one non-peptidyl polymer via the N-terminus. In particular, the immunoglobulin Fc region of the present invention may be in the form of a homodimer, and therefore, linked to one or two non-peptidyl polymers via two N-terminals included in the homodimer of the immunoglobulin Fc region. In this regard, the non-peptidyl polymers may bind to the physiologically active polypeptides, respectively, thereby forming the protein complex.

Accordingly, the protein complex of the present invention may be prepared by linking one or two or more of the non-peptidyl polymer, one or two or more of the physiologically active polypeptide, and one or two or more of the immunoglobulin Fc region via a covalent bond.

In on aspect, this disclosure provides a method for preparing a protein complex with N-terminal selectivity of 90% or higher. Specifically, the protein complex prepared by the method of the present invention may be one, in which one end of the non-peptidyl polymer may be linked to the N-terminus of the immunoglobulin Fc region with N-terminal selectivity of 90% or higher, more specifically 95% or higher, even more specifically 98% or higher, and yet even more specifically 99% or higher, but is not limited thereto.

As used herein, the term "linking with N-terminal selectivity of 90% or higher" means that, in 90% or more of the protein complex prepared by purification of the protein complex fractions obtained by a series of reactions according to the present invention, the non-peptidyl polymer is linked to the N-terminus of the Fc region in a position-specific manner. As used herein, the term "90% or higher" may refer to v/v, w/w, and peak/peak, but is not limited to a particular unit. The yield of the protein complex comprising the non-peptidyl polymer linked to the N-terminus of the Fc region in a position-specific manner may vary by reaction conditions, a reactor of the non-peptidyl polymer, etc.

In Examples of the present invention, it was confirmed that a protein complex with N-terminal selectivity of 90% or higher can be prepared by the method according to the present invention, via preparation of various physiologically active polypeptides, non-peptidyl polymers, and Fc complexes.

The pharmaceutical composition may comprise a protein complex, which includes the physiologically active polypeptide-non-peptidyl polymer-N-terminus of an immunoglobulin Fc region, in an amount of 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit. In one embodiment, the protein complex is a long-acting G-CSF produced by covalent conjugation of a human G-CSF analog and human immunoglobulin G4 (IgG4) Fc fragment, linked via a short 3.4 kDa polyethylene glycol linker also referred to as EFLAPEGRASTIM (Rolontis®). The human IgG4 Fc fragment as the conjugation partner for this G-CSF complex improves its pharmacokinetic (PK) and pharmacodynamic properties.

The pharmaceutical composition may further include a pharmaceutically acceptable excipient.

The pharmaceutical composition of the present invention may be administered via various routes including oral, percutaneous, subcutaneous, intravenous, and intramuscular routes, preferably in the form of an injectable formulation. Further, the pharmaceutical composition of the present invention may be formulated by a method known in the art in order to provide rapid, long-lasting, or delayed release of the active ingredient after administration thereof to a mammal. The formulation may be a tablet, a pill, a powder, a sachet, an elixir, a suspension, an emulsion, a solution, a syrup, an aerosol, a soft or hard gelatin capsule, a sterile injectable solution, or a sterile powder. Examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may further include a filler, an anticoagulant, a lubricant, a wetting agent, a flavoring agent, an emulsifying agent, a preservative, etc.

A practical administration dose of the protein complex of the present invention may be determined by several related factors including the types of diseases to be treated, administration routes, the patient's age, gender, weight, and severity of the illness, as well as by the types of the physiologically active polypeptide as an active component. Since the protein complex of the present invention has excellent blood duration and in vivo potency, it can remarkably reduce the administration dose and frequency of a peptide drug, including the protein complex of the present invention.

In another aspect, this disclosure provides a population of protein complexes, including the protein complex prepared according to the above method in an amount of 90% or higher. As used herein, the terms "population of complex" and "population" may be used interchangeably, and they refer to a group of protein complexes including protein complexes, in which a non-peptidyl polymer is linked to the N-terminus of an Fc region, and/or protein complexes, in which a non-peptidyl polymer is linked to a region other than the N-terminus of an Fc region.

The population may include only the protein complexes, in which a non-peptidyl polymer is linked to the N-terminus of an Fc region, or the protein complexes, in which a non-peptidyl polymer is linked to a region other than the N-terminus of an Fc region. Specifically, the percentage of the protein complexes, in which a non-peptidyl polymer is linked to a region other than the N-terminus of an Fc region, included in the population may be 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

For the purpose of the present invention, the population may refer to a population with an increased percentage of the protein complexes, in which a non-peptidyl polymer is linked to a region other than the N-terminus of an Fc region, by removing impurities, unreacted materials, etc., from the protein complexes prepared thereof. Additionally, the population may refer to one which was prepared by a method for preparing protein complexes with N-terminal selectivity of 90% or higher, but is not limited thereto. The population may be efficiently purified by the method of the present invention.

The present invention is particularly directed to the use of the above-described protein complexes in preventing, alleviating, or treating patient in need thereof having a need in increasing their white blood cell production, count, or are in need of increasing stem cell production by administering to the patient a therapeutically effective amount of a protein complex comprising a modified hG-CSF covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. In one embodiment, the protein complex is EFLAPEGRASTIM (Rolontis®).

In some embodiment, the patient initially receives chemotherapeutic agents or regimens including docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). Regardless, the methodologies described in this invention provides superior clinical and side effect outcomes for patients receiving such a regimen. In one embodiment, TC is administered on Day 1 of each cycle intravenously (IV). Accordingly, Docetaxel is administered at 75 mg/m$^2$ IV infusion and (ii) Cyclophosphamide is administered at 600 mg/m$^2$ IV infusion. Each treatment cycle is 21 days, with up to a maximum of 4 cycles of chemotherapy with optional Cycles 5 and 6. To begin full-dose chemotherapy on Day 1 of any cycle (Day 22 of the previous cycle), patients must show ANC≥1.5×10$^9$/L and a platelet count ≥100×10⁹/L. In some embodiments, the chemotherapeutic regimen is a TAC regimen administered in cycles.

In some embodiments, EFLAPEGRASTIM is administered at 13.2 mg/0.6 mL (containing 3.6 mg G-CSF) fixed dose at second day of each cycle to patients having a weight ranging between 30 kg to about 180 kg or preferably having a weight ranging between 40 to 180 kg. In other embodiments, EFLAPEGRASTIM may be administered on Day 2 of each cycle, approximately 24 hours (±2 hours) after TC chemotherapy at 13.2 mg/0.6 mL (containing 3.6 mg G-CSF) fixed dose.

Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, a "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule. As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference.

The term "recombinant," as used herein, refers to proteins or fragments thereof of the present disclosure created, expressed, isolated, or obtained by technologies or methods known in the art as recombinant DNA technology, which include, e.g., DNA splicing and transgenic expression. The term refers to fusion proteins expressed in a non-human mammal (including transgenic non-human mammals, e.g., transgenic mice), or a cell (e.g., CHO cells) expression system or isolated from a recombinant combinatorial human antibody library.

The term "disease" as used herein is intended to be generally synonymous and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, the term "composition" or "pharmaceutical composition" refers to a mixture of at least one component useful with the presently disclosed fusion protein in combination with other components, such as carriers, stabilizers, diluents, dispersing agents, suspending agents, thickening agents, and/or excipients. The pharmaceutical composition facilitates administration of one or more components of the disclosure to an organism.

As used herein, the terms "treat," "treatment," and "treating" refer to the reduction or amelioration of the progression, severity and/or duration of a proliferative disorder, or the amelioration of one or more symptoms (preferably, one or more discernible symptoms) of a proliferative disorder resulting from the administration of one or more fusion protein of the disclosure. In specific embodiments, the terms "treat," "treatment," and "treating" refer to the amelioration of at least one measurable physical parameter of a proliferative disorder, such as growth of a tumor, not necessarily discernible by the patient. In other embodiments, the terms "treat," "treatment," and "treating" refer to the inhibition of the progression of a proliferative disorder, either physically by, e.g., stabilization of a discernible symptom, physiologically by, e.g., stabilization of a physical parameter, or both. In other embodiments, the terms "treat," "treatment," and "treating" refer to the reduction or stabilization of tumor size or cancerous cell count.

The term "cancer" refers to a disease characterized by the uncontrolled (and often rapid) growth of aberrant cells. Cancer cells can spread locally or through the bloodstream and lymphatic system to other parts of the body. Examples of various cancers are described herein and include, but are not limited to, breast cancer, prostate cancer, ovarian cancer, cervical cancer, skin cancer, pancreatic cancer, colorectal cancer, renal cancer, liver cancer, brain cancer, adrenal gland cancer, autonomic ganglial cancer, biliary tract cancer, bone cancer, endometrial cancer, eye cancer, fallopian tube cancer, genital tract cancers, large intestinal cancer, cancer of the meninges, oesophageal cancer, peritoneal cancer, pituitary cancer, penile cancer, placental cancer, pleura cancer, salivary gland cancer, small intestinal cancer, stomach cancer, testicular cancer, thymus cancer, thyroid cancer, upper aerodigestive cancers, urinary tract cancer, vaginal cancer, vulva cancer, lymphoma, leukemia, lung cancer and the like.

The term "tumor" is used interchangeably with the term "cancer" herein, e.g., both terms encompass solid and liquid, e.g., diffuse or circulating, tumors. As used herein, the term "cancer" or "tumor" includes premalignant, as well as malignant cancers and tumors.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism, such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition that is "substantially free" from Y may be completely free from Y. Where necessary, the word "substantially" may be omitted from the definition.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed by the present disclosure. The upper and lower limits of these smaller ranges may independently be included or excluded in the range, and each range where either, neither, or both limits are included in the smaller ranges is also encompassed by the present disclosure, subject to any specifically excluded limit in the stated range. Where the stated range includes one or both of the limits, ranges excluding either or both of those included limits are also encompassed by the present disclosure.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the present disclosure and does not pose a limitation on the scope of the invention unless otherwise claimed. No language in the specification should be construed as indicating any non-claimed element as essential to the practice of the present disclosure.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise. In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present disclosure. Nothing herein is to be construed as an admission that the present disclosure is not entitled to antedate such publication by virtue of prior disclosure. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

Examples provided here are for illustrative purposes only, and the invention is not intended to be limited by these Examples.

EXAMPLES

Example 1: Preparation of Human Granulocyte Colony Stimulating Factor (G-CSF)-PEG-Fc Complex The $^{17,65S}$G-CSF-PEG-Fc protein complex was prepared using a derivative ($^{17,65}$-G-CSF) prepared by substituting serine for the amino acids at positions 17 and 65 of the native G-CSF and then purified.

1-1. Preparation of $^{17,65S}$G-CSF-PEG Conjugate

ALD-PEG-ALD (IDB, Korea), which is polyethylene glycol (PEG) having a molecular weight of 3.4 kDa and aldehyde reactive groups at both ends thereof, was added to 5 mg/mL of $^{17,65}$S-G-CSF (molecular weight: 18 kDa) dissolved in 100 mM phosphate buffer at a molar ratio of G-CSF:PEG of 1:5 to 1:10. A reducing agent, sodium cyanoborohydride (NaBH$_3$CN, Sigma), was added thereto at a final concentration of 20 mM and allowed to react at 4° C. to 8° C. under slow stirring for about 1 hour. To obtain a conjugate in which PEG is selectively linked to the amino terminus of human granulocyte colony stimulating factor and PEG and G-CSF are linked to each other at a ratio of 1:1, the reaction mixture was subjected to SP HP (GE healthcare, USA) cation exchange chromatography to purify a $^{17,65S}$G-CSF-PEG conjugate with a high purity.

1-2. Preparation of $^{17,65}$G-CSF-PEG-Fc Complex

In order to link the $^{17,65}$G-CSF-PEG conjugate purified in Example 1-1 to the N-terminus of immunoglobulin Fc, the immunoglobulin Fc fragment was added and reacted at a molar ratio of $^{17,65}$Ser-G-CSF-PEG conjugate: immunoglobulin Fc of 1:1 to 1:4. The reaction solution was prepared as a 100 mM phosphate buffer (pH 5.5 to 6.5), and sodium cyanoborohydride (NaCNBH3, Sigma) was added as a reducing agent at a final concentration of 20 mM. The reaction was allowed at 4° C. to 8° C. under slow stirring.
1-3. Isolation and Purification of $^{17,65S}$Ser-G-CSF-PEG-Fc (or $^{17,65S}$G-CSF-PEG-Fc) Complex In order to remove unreacted materials and by-products after the binding reaction of Example 1-2 and to purify the $^{17,65S}$G-CSF-PEG-Fc protein complex thus produced, the reaction mixture was buffer-exchanged to 10 mM Tris (pH 8.0) containing 2 M NaCl and then passed through a Source Phenyl column. To remove impurities, the $^{17,65S}$G-CSF-PEG-Fc protein complex was purified with a concentration gradient of 20 mM Tris (pH 8.0) buffer solution. A small amount of unreacted immunoglobulin Fc and $^{17,65}$G-CSF dimer as impurities were present in the obtained $^{17,65S}$G-CSF-PEG-Fc protein complex fraction. In order to remove the impurities, Q HP (GE healthcare, USA) anion chromatography was further performed. Q HP (GE healthcare, USA) was equilibrated with a 20 mM Tris (pH 8.0) buffer solution, and then the purified $^{17,65S}$G-CSF-PEG-Fc protein complex fraction was applied thereto. Finally, a high-purity $^{17,65S}$G-CSF-PEG-Fc protein complex was purified with a linear concentration gradient of a 20 mM Tris (pH 8.0) buffer solution containing 1 M sodium chloride. N-terminal selectivity of the Fc region of the prepared $^{17,65S}$G-CSF-PEG-Fc protein complex was examined by peptide mapping, and the selectivity was found to be 90% or higher.

Example 2: Preparation of Protein Complex Using PEG with Different Reactive Groups 2-1. Preparation of $^{17,65S}$G-CSF-PEG Conjugate SMB-PEG-SMB (Nektar, USA), which is polyethylene glycol (PEG) having a molecular weight of 3.4 kDa and succinimidyl alpha-methyl butanoate (SMB) reactive groups at both ends thereof, was added to 10 mg/mL of $^{17,65S}$G-CSF (molecular weight 18 kDa) dissolved in 20 mM phosphate buffer (pH 8.0) at a molar ratio of G-CSF:PEG of 1:3, and allowed to react at room temperature under slow stifling for about 30 minutes. To obtain a conjugate in which PEG is selectively linked to the amino terminus of $^{17,65S}$G-CSF and PEG and $^{17,65S}$G-CSF are linked to each other at a ratio of 1:1, the reaction mixture was subjected to SP HP (GE Healthcare, USA) cation exchange chromatography.

2-2. Preparation of $^{17,65S}$G-CSF-PEG-Fc Complex

In order to link the $^{17,65S}$G-CSF-PEG conjugate purified in Example 2-1 to a region other than the N-terminus of immunoglobulin Fc, the immunoglobulin Fc fragment was added and reacted at a molar ratio of $^{17,65S}$G-CSF-PEG conjugate: immunoglobulin Fc of 1:4 to 1:8. The reaction was allowed in 20 mM phosphate buffer (pH 5.5 to 6.5) at room temperature for about 2 hours under slow stifling.

2-3. Isolation and Purification of $^{17,65S}$G-CSF-PEG-Fc Complex

In order to remove unreacted materials and by-products after the binding reaction of Example 2-2 and to purify the $^{17,65S}$G-CSF-PEG-Fc protein complex thus produced, the reaction mixture was passed through a Q HP (GE Healthcare, USA) anion exchange chromatography column and thus unbound Fc was removed and a $^{17,65S}$G-CSF-PEG-Fc protein complex fraction was obtained. The reaction solution was applied to a Q HP column equilibrated with 20 mM Tris (pH 8.0) buffer, and the $^{17,65S}$G-CSF-PEG-Fc protein complex was purified with a concentration gradient of a buffer solution containing 1 M sodium chloride (NaCl). A small amount of unreacted immunoglobulin Fc and $^{17,65S}$G-CSF dimer as impurities was present in the obtained $^{17,65S}$G-CSF-PEG-Fc protein complex fraction. In order to remove the impurities, Source iso (GE Healthcare, USA) hydrophobic chromatography was further performed. Finally, a high-purity $^{17,65S}$G-CSF-PEG-Fc protein complex was purified with a linear concentration gradient of 50 mM Tris (pH 7.5) buffer solution containing 1.2 M ammonium sulfate using Source iso (GE Healthcare, USA). N-terminal selectivity of the Fc region of the prepared $^{17,65S}$G-CSF-PEG-Fc protein complex was examined by peptide mapping, and the selectivity was found to be 90% or higher.

Example 3: Comparison of Efficacy of Complex Depending on Fc Binding Position

The protein complexes prepared in Examples above, $^{17,65S}$G-CSF-PEG-Fc was subjected to in vitro and in vivo efficacy tests, respectively. As shown in the following Tale, binding to the N-terminus (proline) of Fc showed better efficacy than binding to other regions (e.g., lysine).

TABLE 1

In vitro activity-use bone marrow cell proliferation assay of $^{17,65S}$G-CSF-PEG-Fc positional isomers

| Test material | EC50 (ng/ml) | % vs. Experimental group |
|---|---|---|
| $^{17,65S}$G-CSF-(N-terminus)-PEG-(N-Terminus) Fc-Experimental Group | 134.43 | 100.00 |
| $^{17,65S}$G-CSF-(N-terminus)-PEG-(lysine) Fc | 225.87 | 59.50 |

As shown in Table 1, comparison of in vitro activities between $^{17,65S}$G-CSF-(N-terminus)-PEG-(N-Terminus) Fc-Experimental Group S-G-CSF-PEG-Fc positional isomers showed that the $^{17,65S}$G-CSF-(N-terminus)-PEG-(N-Terminus) Fc-Experimental Group S-G-CSF-PEG-Fc complex of the present invention, which was prepared by specific binding to a N-terminus of immunoglobulin Fc fragment, has about 67% increased titer, compared to a $^{17,65S}$G-CSF-(N-terminus)-PEG-(N-Terminus) Fc-Experimental Group S-G-CSF-PEG-Fc complex which was prepared by binding to another position of an immunoglobulin Fc region.

Example 4—Fixed Dose of EFLAPEGRASTIM in Patients Receiving Docetaxel-Cyclophosphamide Chemotherapy Clinical studies of EFLAPEGRASTIM, a long acting G-CSF protein complex, have provided a weight-based dosing approach to manage patient's neutropenia. Dose ranges of 135 μg/kg to 270 μg/kg (36.8 μg/kg to 73.6 μg/kg as G-CSF) have shown clinical activity and were well tolerated. At 270 μg/kg (73.6 μg/kg as G-CSF) EFLAPEGRASTIM, superiority has been demonstrated when compared to pegfilgrastim.

In this study and to simplify treatment and reduce the complications of a weight-based dose, a fixed dose of EFLAPEGRASTIM was studied. To address the possibility that patient weight could affect clinical benefit and/or toxicity, the effect of body weight on ANC response was evaluated. Accordingly, a dose of 13.2 mg (3.6 mg G-CSF) which is equivalent to ~176 μg/kg (48 μg/kg G-CSF) for a 75-kg patient was selected for all patients regardless of their individual weight.

Methodology—The clinical study protocols were reviewed and approved by Independent Review Boards (IRBs) and/or Ethics Committees at respective sites and the studies were conducted in accordance with consensus ethics principles derived applicable standards under 21 CFR Parts 50 and 56 and the World Medical Association Declaration of Helsinki.

The study consisted of 2 phases—screening (30 days) and treatment (4 cycles of 21 days with optional Cycles 5 and 6). The administration of chemotherapy occurred on Day 1 of each cycle: docetaxel 75 mg/m² intravenous (IV) and cyclophosphamide 600 mg/m² IV infusion per institutional standard of care. EFLAPEGRASTIM (3.6 mg G-CSF) was administered on Day 2 of each cycle, about 24 hours after the last dose of chemotherapy.

Eligibility criteria required that study patients to be aged ≥18 years with newly diagnosed, histologically confirmed ESBC, defined as operable Stage I to Stage IIIA breast cancer, who were candidates for adjuvant or neoadjuvant docetaxel and cyclophosphamide chemotherapy. Patients were required to have an Eastern Cooperative Oncology Group (ECOG) Performance Status ≤2. To begin each subsequent cycle of chemotherapy, patients were required to have adequate hematological, renal, and hepatic function as defined by: ANC≥1.5×10⁹/L; platelet count ≥100×10⁹/L; hemoglobin >9 g/dL; calculated creatinine clearance >50 mL/min; aspartate aminotransferase (AST)/serum glutamic-oxaloacetic transaminase (SGOT) and alanine aminotransferase (ALT)/serum glutamic-pyruvic transaminase (SGPT) ≤2.5×upper limit of normal (ULN); alkaline phosphatase ≤2.0×ULN; and total bilirubin ≤1.5 mg/dL.

Patients who had a history of with known sensitivity to *Escherichia coli*-derived products such as L-asparaginase, somatropin growth hormone, or recombinant interferon α-2b; active infection, or ongoing treatment with anti-infectives, prior bone marrow or stem cell transplant, major surgery within 30 days prior to enrollment, or any other malignancy within 5 years prior to enrollment were excluded. Women who were pregnant or breast-feeding were also excluded.

Demographics of the 643 patients enrolled in the 2 other Phase 3 studies are also used as pooled data for further analysis. Such demographics are summarized in Table 2, the results of which were also used in driving the conclusion of the present example. These two Phase 3 studies (ADVANCE and RECOVER) were randomized, comparative, multi-national studies conducted at 82 active sites (US, Canada, South Korea) and 74 active sites (US, Canada, Hungary, Poland, India, South Korea), respectively, and are described in detail elsewhere. (Schwartzberg et al, in press; Cobb et al, submitted) All patients, or their legally authorized representatives, gave written informed consent. These studies evaluated EFLAPEGRASTIM versus pegfilgrastim in the management of chemotherapy-induced neutropenia in patients with ESBC who were receiving docetaxel and cyclophosphamide chemotherapy. There were 3 study phases—screening (30 days), treatment (4 cycles of 21 days), and follow-up (to 12 months from the last dose). Patients were administered IV docetaxel and cyclophosphamide at the doses stated above on Day 1 of each cycle, as in the intensive PK study, before receiving study drug (EFLAPEGRASTIM 3.6 mg G-CSF or pegfilgrastim 6 mg G-CSF) about 24 hours after the last dose of docetaxel and cyclophosphamide chemotherapy.

Bioanalytical Assessments—A validated enzyme-linked immunosorbent assay (ELISA) was used to determine EFLAPEGRASTIM concentration in serum samples. The assay depended on the capturing antibody, biotin-labeled polyclonal antibody (pAb) raised against EFLAPEGRASTIM G-CSF, bound to streptavidin in wells of a StreptaWell 96-well plate. Following blocking and washing steps, EFLAPEGRASTIM in serum samples was then bound to the anti-G-CSF pAb. After incubation and washing, the detection antibody, horseradish peroxidase-conjugated mouse anti-human IgG4, was bound to EFLAPEGRASTIM. After an additional incubation and a washing step, a colorimetric substrate was added. Colorization was stopped, and the optical density of each well was determined using a microplate reader set to 450 nm.

A standard curve was created using a 4-parameter logistic curve-fit over the blank-corrected mean OD values and the nominal EFLAPEGRASTIM standard values. The serum concentrations of EFLAPEGRASTIM were determined from the standard curve. The standard curve was accurate (−1.38%≤% relative error ≤2.43%) and precise (0.21%≤% coefficient of variation ≤4.43%) over the range of 6.25 to 200 ng/mL with a lower limit of quantification of 6.25 ng/mL.

Pharmacokinetic Assessments—PK was subsequently evaluated only in Cycles 1 and 3. PK sampling was performed on Day 2 of Cycle 1 (~24 hours post chemotherapy) within 15 minutes prior to study drug administration and 1, 3, 6, 8, and 10 hours (±15 minutes) following administration of EFLAPEGRASTIM. Samples for PK were also drawn within 15 minutes prior to study drug administration in every cycle and on Days 3, 4, 5, 8, 10, and 15 (±2 hours) in Cycles 1 and 3 to determine the serum concentrations of EFLAPEGRASTIM. The end-of-study visit occurred on Day 35±5 days after the last dose of study drug.

Individual PK parameters were determined by non-compartmental analysis using Phoenix WINNONLIN software (Version 8.2, Certara Corporation, New Jersey) and included maximum serum EFLAPEGRASTIM concentration ($C_{max}$), time of maximum concentration ($T_{max}$), area under the serum concentration-time curve to the last measured concentration ($AUC_{last}$) and to infinity (AUC), apparent total body clearance (CL/F), terminal elimination half-life ($t_{1/2}$), and mean residence time ($MRT_{last}$).

Pharmacodynamic Assessments—Absolute ANC values were evaluated in all 3 studies from Cycle 1 and 3 (predose, and Days 1 to 15). These data were pooled for analysis. Area under the ANC effect curve ($AUEC_{ANC}$) values for Cycle 1 were calculated using Phoenix WINNONLIN software.

Statistical Analysis—the population consisted of all patients who provided blood samples for at least 3 time points for measurement of EFLAPEGRASTIM concentration with predose concentrations <5% of $C_{max}$. Pharmacokinetic data are presented as mean±standard deviation (SD). For analyses of ANC data, the patient population consisted of all patients who were enrolled and received at least 1 dose of any study medication. Pearson's correlation test was used to describe the potential effect of body weight on response to EFLAPEGRASTIM and pegfilgrastim using GraphPad Prism software (Version 8, California). Values of the PK parameters $C_{max}$ and $AUC_{last}$ in Cycles 1 and 3 were compared using a paired t-Test (Excel, Office 2016, Washington). Statistical significance was ascribed to differences of p<0.05. Descriptive analyses of demographic and ANC data were performed using SAS for Windows (version 9.4, North Carolina).

Figure 5:
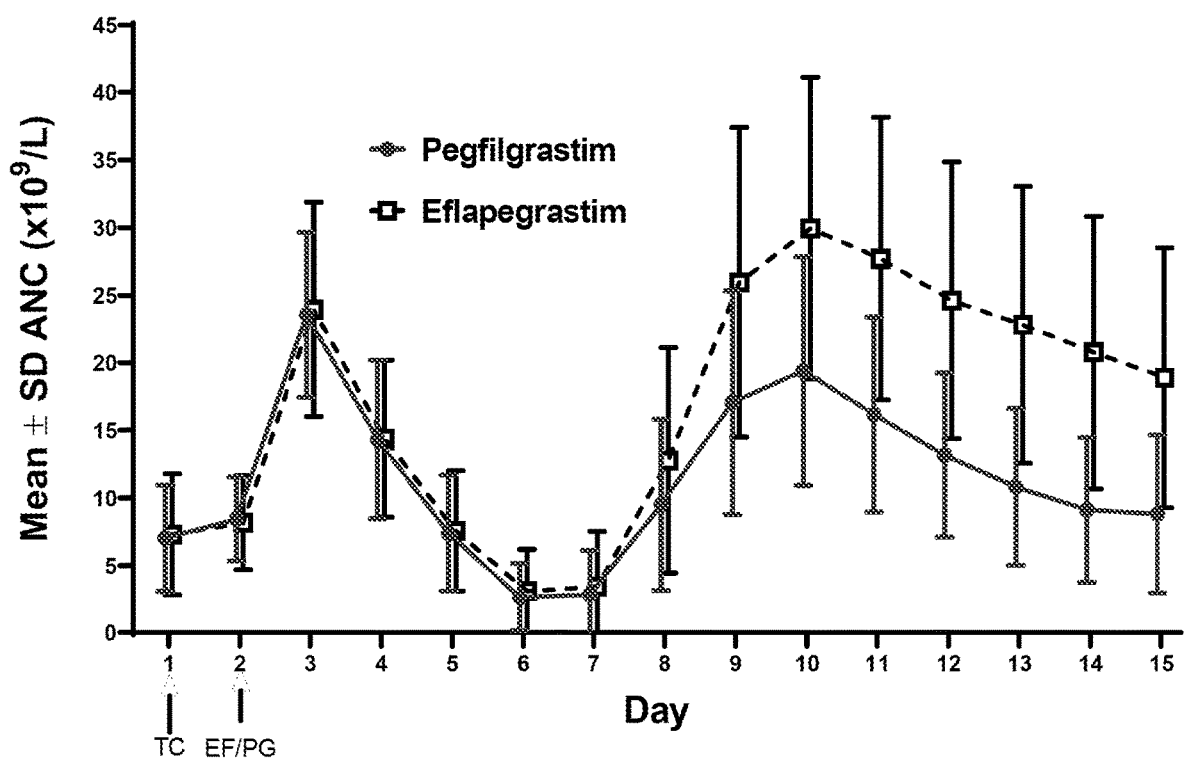
FIG. 5. shows the mean Cycle 1 absolute neutrophil counts±SD after administration of either EFLAPEGRASTIM (N=331) or pegfilgrastim (N=290); pooled data from the 3 studies. EFLAPEGRASTIM was administered ~24 hours after docetaxel and cyclophosphamide chemotherapy. (ANC, absolute neutrophil count; EF, administration of EFLAPEGRASTIM; PG, pegfilgrastim; SD, standard deviation; TC, administration of docetaxel and cyclophosphamide).

A total of 26 female patients participated in the intensive PK study and received at least 1 dose of EFLAPEGRASTIM after docetaxel and cyclophosphamide treatment (Table 2). Of these, 23 patients completed Cycle 4 of the treatment phase (ie, completed the study), and 3 patients withdrew before completing the study (1 patient withdrew because of an adverse event considered unrelated to study drug, 1 patient initiated a non-protocol therapy for the treatment of breast cancer, and 1 patient withdrew consent). The demographics in RECOVER and ADVANCE studies also follow the same pattern as provided herein below. The data analyzed in FIGS. 5 and 6 is based on pooled data from these studies as applicable to the presently claimed invention.

2170±627 mL/h). The $C_{max}$ was 85.1±46.7 ng/mL, ~30% of that in Cycle 1. Similarly, the $AUC_{last}$ was 6950±3420 h·ng/mL, ~32% of that in Cycle 1. The $C_{max}$ and $AUC_{last}$ values in Cycle 3 were significantly lower than in Cycle 1. A summary of EFLAPEGRASTIM PK parameters in Cycle 1 and Cycle 3 is presented in Table 3.

TABLE 2

Demographics

| | Study[a] | | | | |
|---|---|---|---|---|---|
| | PK Study | ADVANCE (Phase 3) (n) | | RECOVER (Phase 3) (n) | |
| | EFLAPEG-RASTIM (26) | EFLAPEG-RASTIM (196) | Pegfilgrastim (210) | EFLAPEG-RASTIM (118) | Pegfilgrastim (119) |
| Age | | | | | |
| Median, years (range) | 56.0 (29-77) | 61 (28-83) | 60 (24-84) | 58 (29-80) | 59 (34-88) |
| <65 years, n (%) | 19 (73) | 118 (60) | 129 (61) | 74 (63) | 79 (66) |
| 65 to <75 years, n (%) | 6 (23) | 65 (33) | 66 (31) | 39 (33) | 26 (22) |
| ≥75 years, n (%) | 1 (4) | 13 (7) | 15 (7) | 5 (4) | 14 (12) |
| Weight, n (%) | | | | | |
| Median, kg (range) | 80.7 (41.8-163.1) | 78.6 (41.5-144.7) | 78.7 (42.4-150.0) | 74.7 (40.3-171.4) | 74.0 (46.0-162.8) |
| Sex, n (%) | | | | | |
| Female | 26 (100) | 195 (99) | 209 (>99) | 118 (100) | 119 (100) |
| Male | 0 | 1 (1) | 1 (<1) | 0 | 0 |
| Race, n (%) | | | | | |
| Caucasian | 20 (77) | 156 (80) | 159 (76) | 85 (72) | 96 (81) |
| Black or African American | 1 (4) | 26 (13) | 32 (15) | 11 (9) | 7 (6) |
| Asian | 1 (4) | 9 (5) | 9 (4) | 20 (17) | 16 (13) |
| American Indian or Alaska Native | 0 | 1 (1) | 1 (<1) | 1 (1) | 0 |
| Native Hawaiian or Other Pac. Islander | 0 | 0 | 1 (<1) | 0 | 0 |
| Other | 4 (15) | 4 (2) | 8 (4) | 1 (1) | 0 |
| ECOG Performance Status, n (%) | | | | | |
| 0 | 5 (19) | 140 (71) | 147 (70) | 99 (84) | 90 (76) |
| 1 | 21 (81) | 56 (29) | 59 (28) | 19 (16) | 27 (23) |
| 2 | 0 | 0 | 4 (2) | 0 | 2 (2) |

[a]EFLAPEGRASTIM was administered as a fixed dose of 3.6 mg G-CSF and pegfilgrastim was administered as a fixed dose of 6 mg G-CSF, both given once per chemotherapy cycle, ~24 hours after docetaxel and cyclophosphamide chemotherapy.
ECOG, Eastern Cooperative Oncology Group; Pac, Pacific; SD, standard deviation.

Figures 2A, 2B:
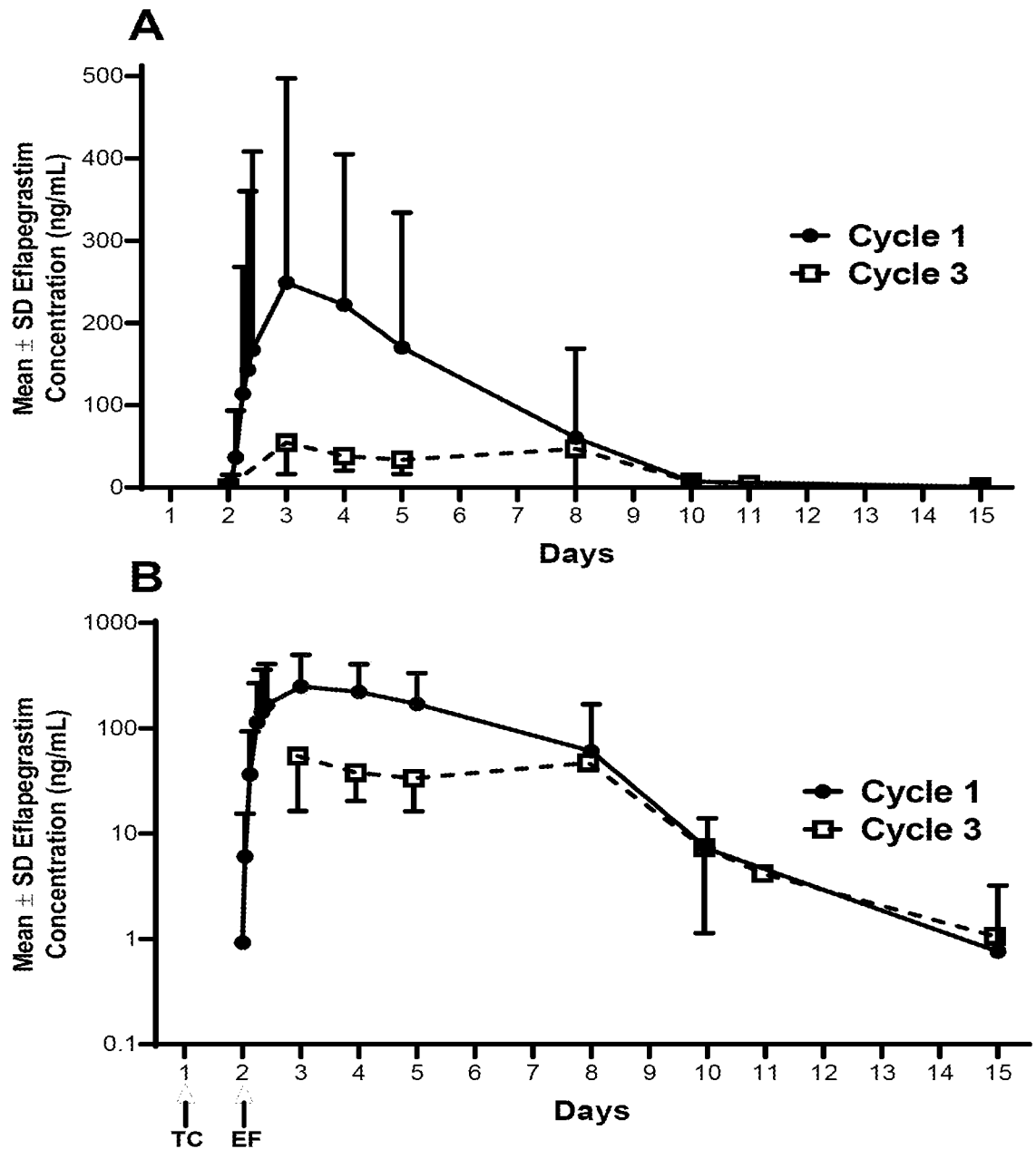
FIGS. 2A and 2B show the mean serum EFLAPEGRASTIM concentrations±SD in the pharmacokinetic study of Example 4 in Cycle 1 and Cycle 3 in 23 ESBC patients in linear scale (FIG. 2A) and in semi-log scale (FIG. 2B). EFLAPEGRASTIM was administered 24 hours after docetaxel and cyclophosphamide chemotherapy. (EF, administration of EFLAPEGRASTIM; SD, standard deviation; TC, administration of docetaxel and cyclophosphamide).

Following administration of EFLAPEGRASTIM in this PK study, quantifiable serum concentrations were observed by 3 hours postdose and, in the majority of patients, remained quantifiable up to Days 8 to 10 (FIG. 2). In Cycle 1, the $C_{max}$ of EFLAPEGRASTIM was 282±250 ng/mL (Table 3) The Cycle 1 $AUC_{last}$ and $AUC_{inf}$ were highly variable (22000±19100 h·ng/mL and 23500±19700 h·ng/mL, respectively). The variability is likely attributable to inter-subject differences in ANC, resulting in differences in neutrophil-mediated clearance. The $MRT_{last}$ was 64.6±17.4 hours and $t_{1/2}$ was 42.1 hours.

In Cycle 3, EFLAPEGRASTIM exposure was lower than the exposure in Cycle 1, with EFLAPEGRASTIM clearance ~3-fold higher in Cycle 3 than in Cycle 1 (818±409 mL/h vs.

TABLE 3

Summary of EFLAPEGRASTIM Noncompartmental Pharmacokinetic Parameters in Cycles 1 and 3 of the Intensive Pharmacokinetic Study (N = 23[a, b])

| PK Parameter | Statistic | Cycle 1[a] | Cycle 3[b] |
|---|---|---|---|
| $C_{max}$ (ng/mL) | Mean | 282 | 85.1 |
| | SD | 250 | 46.7 |
| | Range | 20.5, 1170 | 29.0, 188 |
| $T_{max}$ (h) | Median | 25.00 | 23.88 |
| | Range | 6.00, 143.98 | 1.07, 143.05 |
| $AUC_{last}$ (h · ng/mL) | Mean | 22000 | 6950 |
| | SD | 19100 | 3420 |
| | Range | 2290, 72600 | 2770, 15300 |

TABLE 3-continued

Summary of EFLAPEGRASTIM Noncompartmental
Pharmacokinetic Parameters in Cycles 1 and 3 of the
Intensive Pharmacokinetic Study (N = 23[a, b])

| PK Parameter | Statistic | Cycle 1[a] | Cycle 3[b] |
|---|---|---|---|
| $AUC_{inf}$ | Mean | 23500 | 6470 |
| (h · ng/mL) | SD | 19700 | 1960 |
|  | Range | 8880, 72900 | 4730, 8590 |
| $t_{1/2}$ (h) | Mean | 42.1 | 57.5 |
|  | SD | 27.8 | 5.8 |
|  | Range | 16.1, 115 | 51.2, 62.6 |
| CL/F | Mean | 818 | 2170 |
| (mL/h) | SD | 409 | 627 |
|  | Range | 181, 1490 | 1540, 2790 |
| $MRT_{last}$ (h) | Mean | 64.6 | 90.2 |
|  | SD | 17.4 | 26.6 |
|  | Range | 40.2, 97.9 | 48.9, 136 |

$AUC_{inf}$, area under the time-concentration curve from time 0 extrapolated to infinity; $AUC_{last}$, area under the time-concentration curve from time 0 to the last measurable concentration; $C_{max}$, maximum concentration; SD, standard deviation; CL/F, apparent total body clearance; $MRT_{last}$, mean residence time from time of dose to the time of the last measurable concentration; $t_{1/2}$, terminal phase half-life; $T_{max}$, time of maximum concentration.
[a]Due to the limited number of samples available during the terminal-elimination phase of the EFLAPEGRASTIM profile, $AUC_{inf}$ and $t_{1/2}$ values were only estimable for 10 of 23 patients in Cycle 1.
[b]Due to an insufficient number of samples collected in the terminal-elimination phase of EFLAPEGRASTIM profile, $AUC_{inf}$ and $t_{1/2}$ values could only be determined for 3 of 21 patients in Cycle 3.

Figure 3:
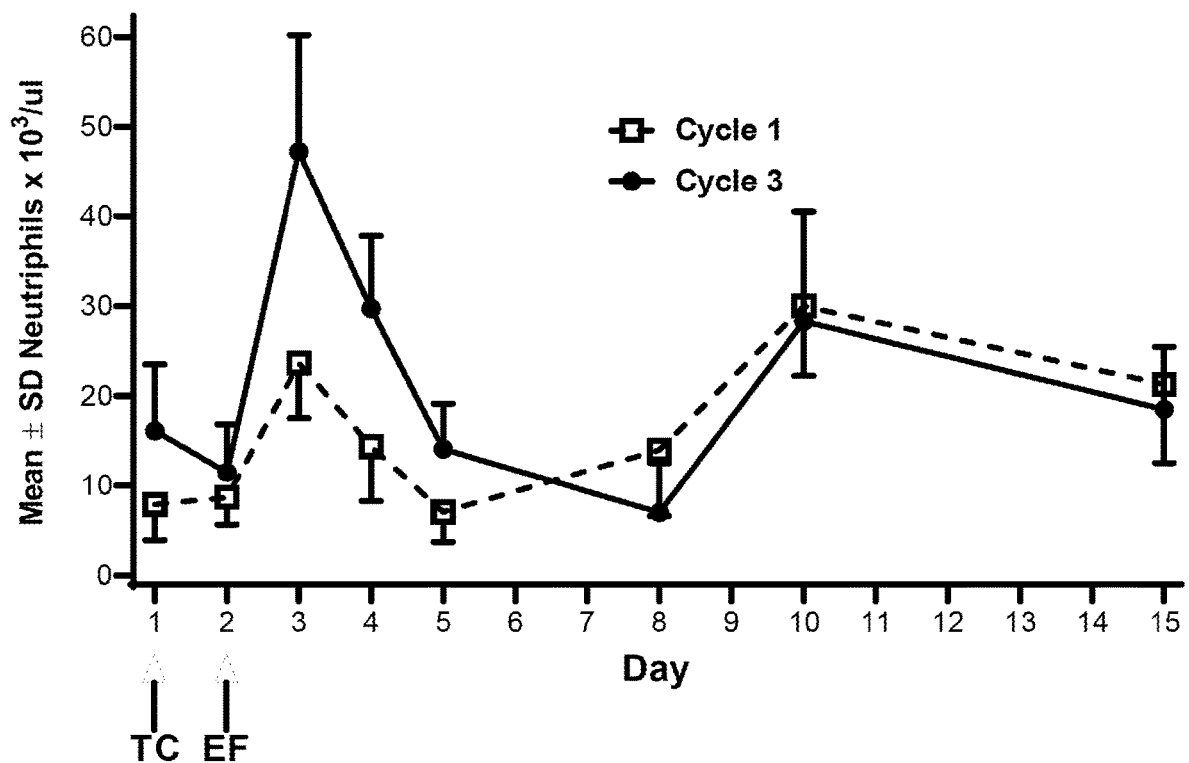
FIG. 3 shows the results of the mean EFLAPEGRASTIM concentrations±SD overlaid with absolute neutrophil count in patients enrolled in the pharmacokinetic study of Example 4 in Cycle 1 and Cycle 3 (N=23). EFLAPEGRASTIM was administered about 24 hours after docetaxel and cyclophosphamide chemotherapy. (TC, administration of docetaxel and cyclophosphamide; EF, administration of EFLAPEGRASTIM; SD, standard deviation).
Figures 4A, 4B:
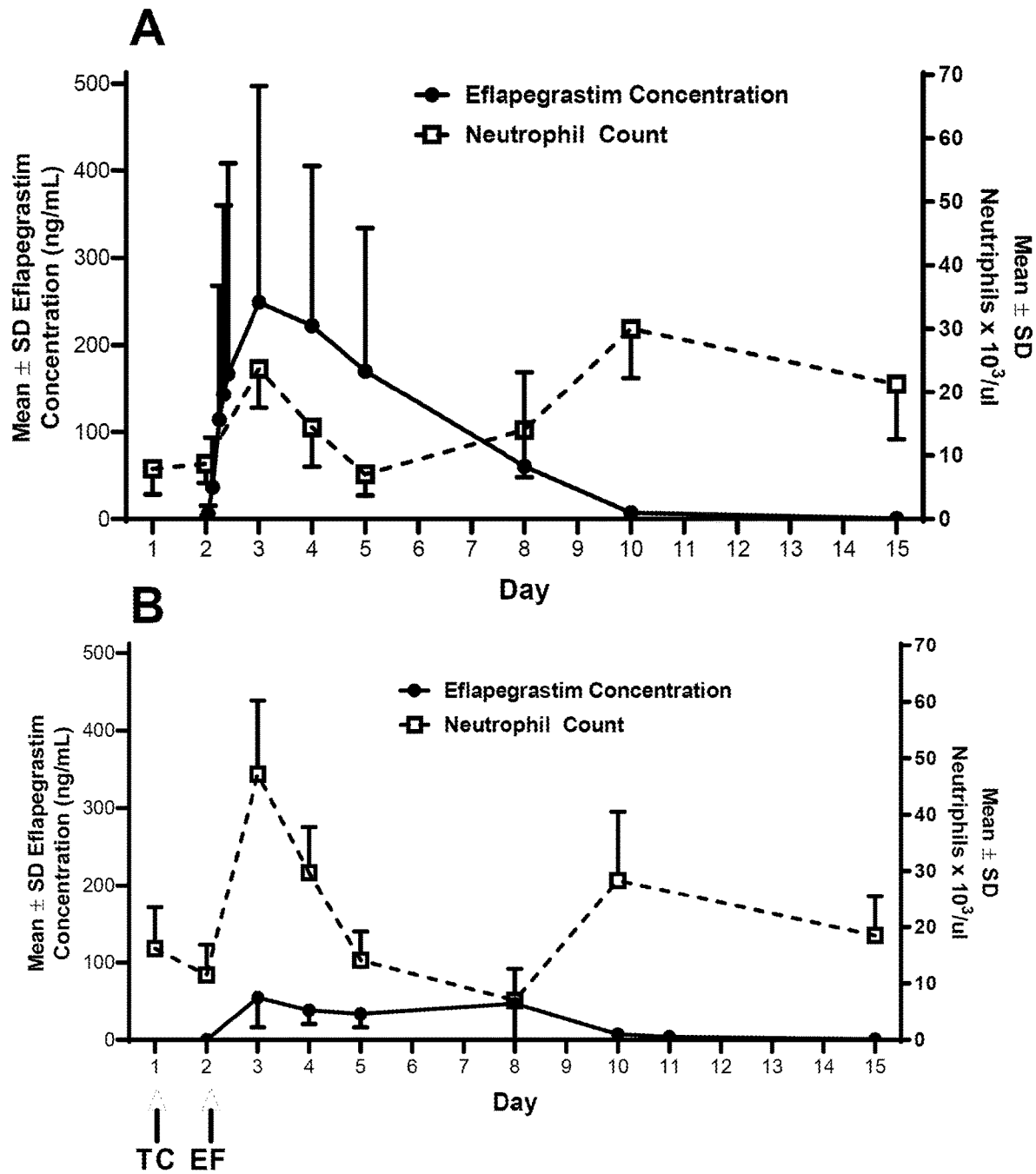
FIGS. 4A and 4B show the mean EFLAPEGRASTIM concentrations±SD overlaid with absolute neutrophil count in patients enrolled in the intensive pharmacokinetic study in Cycle 1 (FIG. 4A) and Cycle 3 (FIG. 4B) (N=23). EFLAPEGRASTIM was administered ~24 hours after docetaxel and cyclophosphamide chemotherapy. (TC, administration of docetaxel and cyclophosphamide; EF, administration of EFLAPEGRASTIM; SD, standard deviation).

In the intensive PK study, the mean predose ANC in Cycle 1 was ~9×10³/μL and the first peak (ANC value ~24×10³/μL) occurred 24 hours after the EFLAPEGRASTIM dose (2 days after chemotherapy) (FIG. 3). The nadir mean ANC on Day 5 of Cycle 1 was ~7×10³/μL, or ~78% of the predose mean ANC. The recovery peak occurred on Day 10, and ANC remained >2-fold above predose values on Day 15. In Cycle 3, the mean predose ANC was ~1.3-fold higher than the Cycle 1 predose mean ANC, and the mean postdose ANC peak on Day 3 was ~1.7-fold higher than in Cycle 1. The mean ANC nadir occurred later, on Day 8 (~50% of the predose mean ANC), and the recovery peak occurrence was similar to Cycle 1, occurring on Day 10.

In Cycles 1 and 3, elimination of EFLAPEGRASTIM increases with mean ANC (FIG. 3). The lower EFLAPEGRASTIM exposure in Cycle 3 was attributed to increased neutrophil-mediated clearance, reflecting the higher ANC levels in Cycle 3 compared to Cycle 1. Accordingly, it is observed that the mean ANC values for EFLAPEGRASTIM were comparable to those of pegfilgrastim for the first 3 days after dosing; however, after Day 8, EFLAPEGRASTIM had a greater effect on ANC recovery than pegfilgrastim. The relationship between body weight and ANC response (i.e., $AUEC_{ANC}$) was evaluated after administration of EFLAPEGRASTIM (3.6 mg G-CSF) or pegfilgrastim (6 mg G-CSF) ~24 hours after administration of chemotherapy in patients with ESBC enrolled in the 3 studies.

FIG. 5 summarizes neutrophil response as a function of body weight. Pearson's correlation test, performed in each treatment arm, showed that body weight did not correlate with $AUEC_{ANC}$ response. These results support administration of EFLAPEGRASTIM as a fixed dose reflecting that the mean duration of severe neutropenia, did not vary as a function of body weight for EFLAPEGRASTIM.

In the present study, EFLAPEGRASTIM was demonstrated to increase neutrophil concentrations following administration ~24 hours after chemotherapy. The nadir mean ANC on Day 7 of Cycle 1 was ~3.5×10³/μL, or ~51% of the predose mean ANC in pooled data. EFLAPEGRASTIM, at a G-CSF dose of 3.6 mg, was found to have a greater effect on ANC recovery than pegfilgrastim at a higher G-CSF dose of 6 mg. The increased potency of EFLAPEGRASTIM suggests that the Fc fragment of EFLAPEGRASTIM increases G-CSF penetration into bone marrow and provides a longer retention of G-CSF in the bone marrow than other G-CSF products such as pegfilgrastim.

EFLAPEGRASTIM systemic exposure, based on $C_{max}$ and $AUC_{last}$, was notably higher in Cycle 1 than in Cycle 3. Because the mean ANC values predose and the peak values postdose were higher in Cycle 3 than Cycle 1, we conclude that neutrophil-mediated clearance of EFLAPEGRASTIM increased in Cycle 3 resulting in decreased drug exposure. Similar effects were observed with pegfilgrastim; increases in neutrophils increased the clearance of the drug. (see e.x. Roskos L K, Lum P, Lockbaum P, Schwab G, Yang B B. Pharmacokinetic/pharmacodynamic modeling of pegfilgrastim in healthy subjects. *J Clin Pharmacol.* 2006; 46(7): 747-757). The relationship between EFLAPEGRASTIM level and ANC is the opposite of what would be expected for a causal relationship (ie, increased exposure would be expected to result in increased ANC or shorter recovery). The concentration-response relationship is confounded by the relationship of ANC to the clearance of EFLAPEGRASTIM. Higher ANC values predict higher clearance, and therefore lower EFLAPEGRASTIM concentrations, confounding any relationship between exposure and ANC response.

The increase in EFLAPEGRASTIM clearance with elevated ANC levels can represent a clinical benefit. As neutrophil levels increase, EFLAPEGRASTIM neutrophil-mediated clearance increases, reducing EFLAPEGRASTIM plasma concentrations. This has the effect of modulating the neutrophil-stimulating response of the drug, decreasing the potential for over-stimulation of neutrophil production. This Example supports that EFLAPEGRASTIM at a fixed dose of 13.2 mg (3.6 mg G-CSF), administered once per chemotherapy cycle, is effective in prophylactic treatment of chemotherapy-induced neutropenia. This conclusion is further supported by the lack of a clinically significant relationship between body weight and response to EFLAPEGRASTIM.

The Examples provided herein supports the superiority of the G-CSF protein complex of the present invention attached the immunoglobulin Fc region through a PEG moiety to increase in vivo duration of the physiologically active polypeptide and to increase or maintain in vivo activity (potency) at the same time.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

What is claimed is:

1. A method of preventing or reducing chemotherapy-induced neutropenia in a patient in need thereof wherein the patient is also being administered at least one cycle of a chemotherapy regimen, the method comprising administering to the patient a EFLAPEGRASTIM at a fixed dose of 13.2 mg regardless of patient's weight approximately 24 hours (±2 hours) after administration of the chemotherapy once per chemotherapy cycle wherein prior to administration of the EFLAPEGRASTIM, the patient exhibits an absolute neutrophil count of ≥1.5×10$^9$/L and a platelet count ≥100×10$^9$/L.

2. The method of claim 1, wherein the neutropenia is severe chronic neutropenia or febrile neutropenia.

3. The method of claim 1, wherein the chemotherapy regimen comprises at least one of docetaxel and cyclophosphamide.

4. The method of claim 1, wherein the chemotherapy regimen comprises a combination of docetaxel and cyclophosphamide.

5. The method of claim 1, wherein a second dose of the EFLAPEGRASTIM is administered between 5 and 30 days after a first dose of EFLAPEGRASTIM is administered to the patient.

6. The method of claim 5, wherein the second dose of the EFLAPEGRASTIM is administered between 15 and 25 days after a first dose of EFLAPEGRASTIM is administered to the patient.

7. The method of claim 1, wherein the patient's weight ranges from 30 kg to 180 kg.

8. The method of claim 1, wherein the fixed dose is provided in a dosage volume of about 0.4 ml to about 1 ml.

9. The method of claim 8, wherein the fixed dose is provided in a dosage volume of about 0.6 ml.

* * * * *